(12) United States Patent
Ainsworth et al.

(10) Patent No.: US 9,814,598 B2
(45) Date of Patent: Nov. 14, 2017

(54) SPINAL IMPLANTS AND IMPLANTATION SYSTEM

(71) Applicant: Quandary Medical, LLC, Denver, CO (US)

(72) Inventors: Stephen D. Ainsworth, Wilmington, NC (US); Eugene E. Avidano, Wilmington, NC (US); Leighton J. LaPierre, Wilmington, NC (US)

(73) Assignee: QUANDARY MEDICAL, LLC, Denver, CO (US)

( * ) Notice: Subject to any disclaimer, the term of this patent is extended or adjusted under 35 U.S.C. 154(b) by 248 days.

(21) Appl. No.: 14/210,065

(22) Filed: Mar. 13, 2014

(65) Prior Publication Data

US 2014/0277499 A1    Sep. 18, 2014

Related U.S. Application Data

(60) Provisional application No. 61/851,976, filed on Mar. 14, 2013.

(51) Int. Cl.
*A61F 2/44* (2006.01)
*A61F 2/46* (2006.01)
(Continued)

(52) U.S. Cl.
CPC ............ *A61F 2/4455* (2013.01); *A61B 17/70* (2013.01); *A61F 2/447* (2013.01); *A61F 2/4465* (2013.01); *A61F 2/4611* (2013.01); *A61F 2002/3023* (2013.01); *A61F 2002/3025* (2013.01); *A61F 2002/3085* (2013.01); *A61F 2002/30092* (2013.01); *A61F 2002/3093* (2013.01);
(Continued)

(58) Field of Classification Search
CPC ...... A61F 2220/0025; A61F 2002/4628; A61F 2002/4629; A61F 2002/30364; A61F 2002/30405; A61B 17/86; A61B 17/025; A61B 17/7098; A61B 17/66; A61B 17/725
USPC .... 606/246–249, 300–330; 623/17.11–17.16
See application file for complete search history.

(56) References Cited

U.S. PATENT DOCUMENTS 1,442,051 A    5/1921    Cummings
1,388,547 A    8/1921    Burns
(Continued)

FOREIGN PATENT DOCUMENTS

DE    3840466    6/1990
DE    9108043    10/1991
(Continued)

OTHER PUBLICATIONS

Japanese Unexamined Patent Publication No. H08-509918, corresponding to WO 94/26177, dated Nov. 24, 1994, Romano.
(Continued)

*Primary Examiner* — Eduardo C Robert
*Assistant Examiner* — Tara R Carter
(74) *Attorney, Agent, or Firm* — Rocky Mountain Patent, LLC

(57) ABSTRACT

Disclosed are surgical implants for providing therapy to a treatment site, tool sets and methods for percutaneously accessing and deploying the implants within the spines. The treatment site may be a vertebral body, disc, and/or motion segments in the lumbar and sacral regions of the spine.

13 Claims, 30 Drawing Sheets

(51) Int. Cl.
*A61B 17/70* (2006.01)
*A61F 2/30* (2006.01)

(52) U.S. Cl.
CPC .............. *A61F 2002/30143* (2013.01); *A61F 2002/30171* (2013.01); *A61F 2002/30235* (2013.01); *A61F 2002/30242* (2013.01); *A61F 2002/30266* (2013.01); *A61F 2002/30309* (2013.01); *A61F 2002/30331* (2013.01); *A61F 2002/30387* (2013.01); *A61F 2002/30405* (2013.01); *A61F 2002/30462* (2013.01); *A61F 2002/30538* (2013.01); *A61F 2002/30545* (2013.01); *A61F 2002/30565* (2013.01); *A61F 2002/30579* (2013.01); *A61F 2002/30601* (2013.01); *A61F 2002/30604* (2013.01); *A61F 2002/30772* (2013.01); *A61F 2002/30784* (2013.01); *A61F 2002/30785* (2013.01); *A61F 2002/30884* (2013.01); *A61F 2002/30891* (2013.01); *A61F 2002/30904* (2013.01); *A61F 2002/30995* (2013.01); *A61F 2002/448* (2013.01); *A61F 2002/4415* (2013.01); *A61F 2002/4475* (2013.01); *A61F 2310/00017* (2013.01); *A61F 2310/00023* (2013.01); *A61F 2310/00029* (2013.01); *A61F 2310/00131* (2013.01); *A61F 2310/00161* (2013.01); *A61F 2310/00359* (2013.01)

(56) References Cited

U.S. PATENT DOCUMENTS

| | | | |
|---|---|---|---|
| 1,630,239 A | 5/1924 | Binkley et al. |
| 2,317,648 A | 4/1943 | Siqveland |
| 2,336,338 A | 12/1943 | Zublin |
| 2,730,101 A | 1/1956 | Hoffman |
| 3,103,926 A | 9/1963 | Cochran et al. |
| 3,367,326 A | 2/1968 | Frazier |
| 3,454,006 A | 7/1969 | Langdon |
| 3,554,192 A | 1/1971 | Isberner |
| 3,620,216 A | 11/1971 | Szymanski |
| 3,788,320 A | 1/1974 | Dye |
| 3,867,728 A | 2/1975 | Stubstad |
| 3,875,595 A | 4/1975 | Froning |
| 3,892,232 A | 7/1975 | Neufeld |
| 4,046,144 A | 9/1977 | McFarlane |
| 4,135,506 A | 1/1979 | Ulrich |
| 4,170,990 A | 10/1979 | Baumgart et al. |
| 4,175,555 A | 11/1979 | Herbert |
| 4,265,231 A | 5/1981 | Scheller, Jr. et al. |
| 4,309,777 A | 1/1982 | Patil |
| 4,349,921 A | 9/1982 | Kuntz |
| 4,401,112 A | 8/1983 | Rezaian |
| 4,446,578 A | 5/1984 | Perkins et al. |
| 4,453,539 A | 6/1984 | Raftopoulos et al. |
| 4,518,383 A | 5/1985 | Evans |
| 4,541,423 A | 9/1985 | Barber |
| 4,545,374 A | 10/1985 | Jacobson |
| 4,553,273 A | 11/1985 | Wu |
| 4,554,914 A | 11/1985 | Kapp et al. |
| 4,573,448 A | 3/1986 | Kambin |
| 4,609,370 A | 9/1986 | Morrison |
| 4,636,217 A | 1/1987 | Ogilvie et al. |
| 4,636,271 A | 1/1987 | Gandolfo |
| 4,640,271 A | 2/1987 | Lower |
| 4,650,466 A | 3/1987 | Luther |
| 4,654,030 A | 3/1987 | Moll et al. |
| 4,657,550 A | 4/1987 | Daher |
| 4,756,649 A | 7/1988 | Heule |
| 4,759,766 A | 7/1988 | Buettner-Janz et al. |
| 4,772,266 A | 9/1988 | Groshong |
| 4,773,402 A | 9/1988 | Asher et al. |
| 4,815,453 A | 3/1989 | Cotrel |
| 4,844,088 A | 7/1989 | Kambin |
| 4,858,601 A | 8/1989 | Glisson |
| 4,862,891 A | 9/1989 | Smith |
| 4,863,477 A | 9/1989 | Monson |
| 4,872,451 A | 10/1989 | Moore et al. |
| 4,874,389 A | 10/1989 | Downey |
| 4,904,260 A | 2/1990 | Ray et al. |
| 4,911,718 A | 3/1990 | Lee et al. |
| 4,932,969 A | 6/1990 | Frey et al. |
| RE33,258 E | 7/1990 | Onik et al. |
| 4,946,378 A | 8/1990 | Hirayama et al. |
| RE33,348 E | 9/1990 | Lower |
| 4,966,604 A | 10/1990 | Reiss |
| 4,969,888 A | 11/1990 | Scholten et al. |
| 4,997,432 A | 3/1991 | Keller |
| 5,002,546 A | 3/1991 | Romano |
| 5,009,659 A | 4/1991 | Hamlin et al. |
| 5,015,255 A | 5/1991 | Kuslich |
| 5,019,079 A | 5/1991 | Ross |
| 5,030,201 A | 7/1991 | Palestrant |
| 5,047,055 A | 9/1991 | Bao |
| 5,059,193 A | 10/1991 | Kuslich |
| 5,062,850 A | 11/1991 | Macmillan et al. |
| 5,071,437 A | 12/1991 | Steffee |
| 5,131,382 A | 7/1992 | Meyer |
| 5,147,404 A | 9/1992 | Downey |
| 5,169,387 A | 12/1992 | Kronner |
| 5,171,279 A | 12/1992 | Mathews |
| 5,171,280 A | 12/1992 | Baumgartner |
| 5,190,546 A | 3/1993 | Jervis |
| 5,192,326 A | 3/1993 | Bao et al. |
| 5,195,968 A | 3/1993 | Lundquist et al. |
| 5,231,910 A | 8/1993 | Harsch et al. |
| 5,236,460 A | 8/1993 | Barber |
| 5,242,443 A | 9/1993 | Kambin |
| 5,242,444 A | 9/1993 | MacMillan |
| 5,242,461 A | 9/1993 | Kortenbach et al. |
| 5,246,458 A | 9/1993 | Graham |
| 5,258,031 A | 11/1993 | Salib et al. |
| 5,261,888 A | 11/1993 | Semm |
| 5,269,785 A | 12/1993 | Bonutti |
| 5,285,795 A | 2/1994 | Ryan et al. |
| 5,290,247 A | 3/1994 | Crittenden |
| 5,290,289 A | 3/1994 | Sanders et al. |
| 5,309,896 A | 5/1994 | Moll et al. |
| 5,313,962 A | 5/1994 | Obenchain |
| 5,336,223 A | 8/1994 | Rogers |
| 5,357,983 A | 10/1994 | Mathews |
| 5,360,448 A | 11/1994 | Thramann |
| 5,366,457 A | 11/1994 | McGuire et al. |
| 5,376,094 A | 12/1994 | Kline |
| 5,383,884 A | 1/1995 | Summers |
| 5,395,188 A | 3/1995 | Bailey et al. |
| 5,395,317 A | 3/1995 | Kambin |
| 5,396,880 A | 3/1995 | Kagan et al. |
| 5,403,276 A | 4/1995 | Schechter et al. |
| 5,415,661 A | 5/1995 | Holmes |
| 5,423,816 A | 6/1995 | Lin |
| 5,433,739 A | 7/1995 | Sluijter et al. |
| 5,437,661 A | 8/1995 | Rieser |
| 5,445,140 A | 8/1995 | Tovey |
| 5,445,619 A | 8/1995 | Burns |
| 5,445,639 A | 8/1995 | Kuslich |
| 5,458,642 A | 10/1995 | Beer et al. |
| 5,458,643 A | 10/1995 | Oka et al. |
| 5,476,467 A | 12/1995 | Benoist |
| 5,478,328 A | 12/1995 | Silverman et al. |
| 5,480,440 A | 1/1996 | Kambin |
| 5,484,437 A | 1/1996 | Michelson |
| 5,489,308 A | 2/1996 | Kuslich et al. |
| 5,496,322 A | 3/1996 | Mathews |
| 5,496,326 A | 3/1996 | Johnson |
| 5,496,338 A | 3/1996 | Miyagi et al. |
| 5,505,732 A | 4/1996 | Michelson |
| 5,514,137 A | 5/1996 | Coutts |
| 5,514,180 A | 5/1996 | Heggeness et al. |
| 5,520,688 A | 5/1996 | Lin |
| 5,534,028 A | 7/1996 | Bao et al. |
| 5,534,031 A | 7/1996 | Matsuzaki et al. |
| 5,535,756 A | 7/1996 | Parasher |

(56) References Cited

U.S. PATENT DOCUMENTS

| | | |
|---|---|---|
| 5,545,228 A | 8/1996 | Kambin |
| 5,545,229 A | 8/1996 | Parsons et al. |
| 5,549,679 A | 8/1996 | Kuslich |
| 5,554,163 A | 9/1996 | Shturman |
| 5,556,429 A | 9/1996 | Felt |
| 5,558,674 A | 9/1996 | Heggeness et al. |
| 5,562,736 A | 10/1996 | Ray et al. |
| 5,569,248 A | 10/1996 | Mathews |
| 5,571,189 A | 11/1996 | Kuslich |
| 5,571,190 A | 11/1996 | Ulrich et al. |
| 5,571,192 A | 11/1996 | Schonhoffer |
| 5,584,887 A | 12/1996 | Kambin |
| 5,591,170 A | 1/1997 | Spievack et al. |
| 5,591,235 A | 1/1997 | Kuslich |
| 5,593,407 A | 1/1997 | Reis |
| 5,630,816 A | 5/1997 | Kambin |
| 5,645,597 A | 7/1997 | Krapiva |
| 5,653,708 A | 8/1997 | Howland |
| 5,658,286 A | 8/1997 | Sava |
| 5,665,122 A | 9/1997 | Kambin |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,690,636 A | 11/1997 | Wildgoose et al. |
| 5,700,291 A | 12/1997 | Kuslich et al. |
| 5,702,449 A | 12/1997 | McKay |
| 5,702,453 A | 12/1997 | Rabbe et al. |
| 5,702,454 A | 12/1997 | Baumgartner |
| 5,702,455 A | 12/1997 | Saggar |
| 5,713,904 A | 2/1998 | Errico et al. |
| 5,720,749 A | 2/1998 | Rupp |
| 5,728,097 A | 3/1998 | Mathews |
| 5,733,260 A | 3/1998 | Demaio et al. |
| 5,733,284 A | 3/1998 | Martin |
| 5,735,813 A | 4/1998 | Lewis |
| 5,735,899 A | 4/1998 | Schwartz et al. |
| 5,741,253 A | 4/1998 | Michelson |
| 5,741,261 A | 4/1998 | Moskovitz et al. |
| 5,743,912 A | 4/1998 | Lahille et al. |
| 5,762,629 A | 6/1998 | Kambin |
| 5,779,704 A | 7/1998 | Kim |
| 5,785,707 A | 7/1998 | Boyd et al. |
| 5,785,709 A | 7/1998 | Kummer et al. |
| 5,787,591 A | 8/1998 | Lu |
| 5,792,044 A | 8/1998 | Foley et al. |
| 5,792,110 A | 8/1998 | Cunningham |
| 5,807,318 A | 9/1998 | St. Goar et al. |
| 5,807,338 A | 9/1998 | Smith et al. |
| 5,810,815 A | 9/1998 | Morales |
| 5,824,093 A | 10/1998 | Ray et al. |
| 5,827,285 A | 10/1998 | Bramlet |
| 5,827,328 A | 10/1998 | Buttermann |
| 5,865,845 A | 2/1999 | Thalgott |
| 5,882,329 A | 3/1999 | Patterson et al. |
| 5,885,292 A | 3/1999 | Moskovitz et al. |
| 5,888,220 A | 3/1999 | Felt et al. |
| 5,888,223 A | 3/1999 | Bray, Jr. |
| 5,891,147 A | 4/1999 | Moskovitz et al. |
| 5,902,231 A | 5/1999 | Foley et al. |
| 5,902,279 A | 5/1999 | Powles et al. |
| 5,906,616 A | 5/1999 | Pavlov et al. |
| 5,916,208 A | 6/1999 | Luther et al. |
| 5,916,267 A | 6/1999 | Tienboon |
| 5,919,172 A | 7/1999 | Golba, Jr. |
| 5,921,971 A | 7/1999 | Agro et al. |
| 5,928,239 A | 7/1999 | Mirza |
| 5,928,284 A | 7/1999 | Mehdizadeh |
| 5,935,131 A | 8/1999 | Bonutti |
| 5,937,524 A | 8/1999 | Hornsby |
| 5,951,553 A | 9/1999 | Betz et al. |
| 5,954,635 A | 9/1999 | Foley et al. |
| 5,954,671 A | 9/1999 | O'Neil |
| 5,961,329 A | 10/1999 | Stucki-McCormick |
| 5,964,761 A | 10/1999 | Kambin |
| 5,968,062 A | 10/1999 | Thomas et al. |
| 5,972,015 A | 10/1999 | Scribner et al. |
| 5,976,146 A | 11/1999 | Ogawa et al. |
| 5,976,186 A | 11/1999 | Bao et al. |
| 5,976,187 A | 11/1999 | Richelsoph |
| 5,980,504 A | 11/1999 | Sharkey et al. |
| 5,989,256 A | 11/1999 | Kuslich et al. |
| 5,989,290 A | 11/1999 | Biedermann et al. |
| 6,001,101 A | 12/1999 | Augagneur et al. |
| 6,001,130 A | 12/1999 | Bryan et al. |
| 6,007,487 A | 12/1999 | Foley et al. |
| 6,010,495 A | 1/2000 | Tilton, Jr. |
| 6,010,502 A | 1/2000 | Bagby |
| 6,019,792 A | 2/2000 | Cauthen |
| 6,022,362 A | 2/2000 | Lee et al. |
| 6,022,376 A | 2/2000 | Assell et al. |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,407 A | 3/2000 | Behrens |
| 6,036,696 A | 3/2000 | Lambrecht et al. |
| 6,053,916 A | 4/2000 | Moore |
| 6,056,749 A | 5/2000 | Kuslich |
| 6,063,088 A | 5/2000 | Winslow |
| 6,066,152 A | 5/2000 | Strauss et al. |
| 6,066,154 A | 5/2000 | Reiley et al. |
| 6,080,099 A | 6/2000 | Slater et al. |
| 6,086,589 A | 7/2000 | Kuslich et al. |
| 6,093,205 A | 7/2000 | McLeod |
| 6,093,207 A | 7/2000 | Pisharodi |
| 6,095,149 A | 8/2000 | Sharkey et al. |
| 6,096,038 A | 8/2000 | Michelson |
| 6,110,210 A | 8/2000 | Norton et al. |
| RE36,857 E | 9/2000 | Euteneuer et al. |
| 6,120,502 A | 9/2000 | Michelson |
| 6,123,705 A | 9/2000 | Michelson |
| 6,127,597 A | 10/2000 | Beyar et al. |
| 6,129,763 A * | 10/2000 | Chauvin ............... A61F 2/4455 623/17.11 |
| 6,132,465 A | 10/2000 | Ray et al. |
| 6,140,452 A | 10/2000 | Felt et al. |
| 6,146,422 A | 11/2000 | Lawson |
| 6,152,871 A | 11/2000 | Foley et al. |
| 6,156,067 A | 12/2000 | Bryan et al. |
| 6,159,179 A | 12/2000 | Simonson |
| 6,159,212 A | 12/2000 | Schoedinger, III et al. |
| 6,159,214 A | 12/2000 | Michelson |
| 6,162,170 A | 12/2000 | Foley et al. |
| 6,171,236 B1 | 1/2001 | Bonutti |
| 6,175,758 B1 | 1/2001 | Kambin |
| 6,176,823 B1 | 1/2001 | Foley et al. |
| 6,187,000 B1 | 2/2001 | Davison et al. |
| 6,187,043 B1 | 2/2001 | Ledergerber |
| 6,187,048 B1 | 2/2001 | Milner et al. |
| 6,206,822 B1 | 3/2001 | Foley et al. |
| 6,206,826 B1 | 3/2001 | Mathews et al. |
| 6,210,412 B1 | 4/2001 | Michelson |
| 6,217,509 B1 | 4/2001 | Foley et al. |
| 6,221,082 B1 | 4/2001 | Marino et al. |
| 6,224,595 B1 | 5/2001 | Michelson |
| 6,224,603 B1 | 5/2001 | Marino |
| 6,224,630 B1 | 5/2001 | Bao et al. |
| 6,231,609 B1 | 5/2001 | Mehdizadeh |
| 6,240,926 B1 | 6/2001 | Chin Gan et al. |
| 6,241,734 B1 | 6/2001 | Scribner et al. |
| 6,241,735 B1 | 6/2001 | Marmulla |
| 6,251,140 B1 | 6/2001 | Marino et al. |
| 6,258,044 B1 | 7/2001 | Lonky et al. |
| 6,264,656 B1 | 7/2001 | Michelson |
| 6,264,695 B1 | 7/2001 | Stoy |
| 6,270,498 B1 | 8/2001 | Michelson |
| 6,280,191 B1 | 8/2001 | Gordon |
| 6,280,447 B1 | 8/2001 | Marino et al. |
| 6,280,475 B1 | 8/2001 | Bao et al. |
| 6,287,313 B1 | 9/2001 | Sasso |
| 6,290,724 B1 | 9/2001 | Marino |
| 6,299,615 B1 | 10/2001 | Huebner |
| 6,306,140 B1 | 10/2001 | Siddiqui |

(56) References Cited

U.S. PATENT DOCUMENTS

| | | |
|---|---|---|
| 6,306,143 B1 | 10/2001 | Kvarnstrom et al. |
| 6,306,177 B1 | 10/2001 | Felt et al. |
| 6,312,443 B1 | 11/2001 | Stone |
| 6,315,795 B1 | 11/2001 | Scarborough et al. |
| 6,319,254 B1 | 11/2001 | Giet et al. |
| RE37,479 E | 12/2001 | Kuslich |
| 6,332,894 B1 | 12/2001 | Stalcup et al. |
| 6,348,055 B1 | 2/2002 | Preissman |
| 6,368,325 B1 | 4/2002 | Mckinley et al. |
| 6,371,968 B1 | 4/2002 | Kogasaka et al. |
| 6,371,990 B1 | 4/2002 | Ferree |
| 6,375,682 B1 | 4/2002 | Fleischmann et al. |
| 6,379,334 B1 | 4/2002 | Frassica |
| 6,383,188 B2 | 5/2002 | Kuslich et al. |
| 6,383,190 B1 | 5/2002 | Preissman |
| 6,387,070 B1 | 5/2002 | Marino et al. |
| 6,387,130 B1 | 5/2002 | Stone et al. |
| 6,395,007 B1 | 5/2002 | Bhatnager et al. |
| 6,395,032 B1 | 5/2002 | Gauchet |
| 6,395,034 B1 | 5/2002 | Suddaby |
| 6,402,750 B1 | 6/2002 | Atkinson et al. |
| 6,402,784 B1 | 6/2002 | Wardlaw |
| 6,409,766 B1 | 6/2002 | Brett |
| 6,416,515 B1 | 7/2002 | Wagner |
| 6,419,639 B2 | 7/2002 | Walther et al. |
| 6,419,677 B2 | 7/2002 | Zucherman et al. |
| 6,419,678 B1 | 7/2002 | Asfora |
| 6,419,704 B1 | 7/2002 | Ferree |
| 6,423,095 B1 | 7/2002 | Van Hoeck et al. |
| 6,428,576 B1 | 8/2002 | Haldimann |
| 6,436,098 B1 | 8/2002 | Michelson |
| 6,436,102 B1 | 8/2002 | Ralph et al. |
| 6,436,119 B1 | 8/2002 | Erb et al. |
| 6,436,140 B1 | 8/2002 | Liu et al. |
| 6,436,143 B1 | 8/2002 | Ross et al. |
| 6,440,138 B1 | 8/2002 | Reiley et al. |
| 6,443,988 B2 | 9/2002 | Felt et al. |
| 6,447,514 B1 | 9/2002 | Stalcup et al. |
| 6,447,518 B1 | 9/2002 | Krause et al. |
| 6,447,546 B1 | 9/2002 | Bramlet et al. |
| 6,447,547 B1 | 9/2002 | Michelson |
| 6,450,986 B1 | 9/2002 | Binner et al. |
| 6,451,057 B1 * | 9/2002 | Chen ............ A61F 2/446 623/17.15 |
| 6,454,807 B1 * | 9/2002 | Jackson ............ A61F 2/447 623/17.15 |
| 6,458,139 B1 | 10/2002 | Palmer et al. |
| 6,464,713 B2 | 10/2002 | Bonutti |
| 6,468,277 B1 | 10/2002 | Justin et al. |
| 6,468,279 B1 | 10/2002 | Reo |
| 6,482,234 B1 | 11/2002 | Weber et al. |
| 6,482,235 B1 | 11/2002 | Lambrecht et al. |
| 6,485,518 B1 | 11/2002 | Cornwall et al. |
| 6,488,710 B2 | 12/2002 | Besselink |
| 6,491,626 B1 | 12/2002 | Stone et al. |
| 6,500,173 B2 | 12/2002 | Underwood et al. |
| 6,517,541 B1 | 2/2003 | Sesic |
| 6,520,992 B1 | 2/2003 | Zollner et al. |
| 6,530,930 B1 | 3/2003 | Marino et al. |
| 6,533,791 B1 | 3/2003 | Betz et al. |
| 6,540,747 B1 | 4/2003 | Marino |
| 6,540,752 B1 | 4/2003 | Hicken et al. |
| 6,558,309 B2 | 5/2003 | Hogendijk et al. |
| 6,558,386 B1 | 5/2003 | Cragg |
| 6,558,390 B2 | 5/2003 | Cragg |
| 6,562,046 B2 | 5/2003 | Sasso |
| 6,572,593 B1 | 6/2003 | Daum |
| 6,574,868 B1 | 6/2003 | Overholt |
| 6,575,979 B1 | 6/2003 | Cragg |
| 6,582,441 B1 | 6/2003 | He et al. |
| 6,607,530 B1 | 8/2003 | Carl et al. |
| 6,610,091 B1 | 8/2003 | Reiley |
| 6,641,564 B1 | 11/2003 | Kraus |
| 6,652,535 B2 | 11/2003 | Kvarnstrom et al. |
| 6,669,699 B2 | 12/2003 | Ralph et al. |
| 6,692,495 B1 | 2/2004 | Zacouto |
| 6,719,797 B1 | 4/2004 | Ferree |
| 6,740,090 B1 | 5/2004 | Cragg et al. |
| 6,746,451 B2 | 6/2004 | Middleton et al. |
| 6,764,489 B2 | 7/2004 | Ferree |
| 6,770,070 B1 | 8/2004 | Balbierz |
| 6,790,210 B1 | 9/2004 | Cragg et al. |
| 6,793,656 B1 | 9/2004 | Mathews |
| 6,805,697 B1 | 10/2004 | Helm et al. |
| 6,821,276 B2 | 11/2004 | Lambrecht et al. |
| 6,875,215 B2 | 4/2005 | Taras et al. |
| 6,896,202 B1 | 5/2005 | Fugere |
| 6,899,716 B2 | 5/2005 | Cragg |
| 6,921,403 B2 | 7/2005 | Cragg et al. |
| 6,991,653 B2 | 1/2006 | White et al. |
| 7,001,396 B2 | 2/2006 | Glazier et al. |
| 7,014,633 B2 | 3/2006 | Cragg |
| 7,025,746 B2 | 4/2006 | Tal |
| 7,033,394 B2 | 4/2006 | Michelson |
| 7,037,309 B2 | 5/2006 | Weil et al. |
| 7,052,500 B2 | 5/2006 | Bashiri et al. |
| 7,063,703 B2 | 6/2006 | Reo |
| 7,087,056 B2 | 8/2006 | Vaughan |
| 7,087,058 B2 | 8/2006 | Cragg |
| 7,128,760 B2 | 10/2006 | Michelson |
| 7,175,626 B2 | 2/2007 | Neff |
| 7,309,338 B2 | 12/2007 | Cragg |
| 7,329,259 B2 | 2/2008 | Cragg |
| 7,465,304 B1 | 12/2008 | Haufe et al. |
| 7,473,256 B2 | 1/2009 | Assell et al. |
| 7,491,236 B2 | 2/2009 | Cragg et al. |
| 7,500,977 B2 | 3/2009 | Assell et al. |
| 7,530,993 B2 | 5/2009 | Assell et al. |
| 7,547,317 B2 | 6/2009 | Cragg |
| 7,547,324 B2 | 6/2009 | Cragg et al. |
| 7,569,056 B2 | 8/2009 | Cragg et al. |
| 7,588,574 B2 | 9/2009 | Assell et al. |
| 7,601,171 B2 | 10/2009 | Ainsworth et al. |
| 7,608,077 B2 | 10/2009 | Cragg |
| 7,632,274 B2 | 12/2009 | Assell |
| 7,641,657 B2 | 1/2010 | Cragg |
| 7,662,173 B2 | 2/2010 | Cragg et al. |
| 7,727,263 B2 | 6/2010 | Cragg |
| 7,740,633 B2 | 6/2010 | Assell et al. |
| 7,744,599 B2 | 6/2010 | Cragg |
| 7,763,025 B2 | 7/2010 | Assell et al. |
| 7,794,463 B2 | 9/2010 | Cragg |
| 7,799,032 B2 | 9/2010 | Assell et al. |
| 7,799,033 B2 | 9/2010 | Assell et al. |
| 7,914,535 B2 | 3/2011 | Assell et al. |
| 8,034,055 B2 | 10/2011 | Cragg |
| 8,052,613 B2 | 11/2011 | Assell et al. |
| 8,105,365 B2 | 1/2012 | Cragg |
| 8,292,928 B2 | 10/2012 | Cragg |
| 8,308,777 B2 | 11/2012 | Assell et al. |
| 8,317,867 B2 | 11/2012 | Cragg |
| 2001/0004710 A1 | 6/2001 | Felt et al. |
| 2001/0032020 A1 | 10/2001 | Besselink |
| 2001/0034495 A1 | 10/2001 | Wilson et al. |
| 2001/0034525 A1 | 10/2001 | Staehlin et al. |
| 2002/0016604 A1 | 2/2002 | Boock et al. |
| 2002/0022888 A1 | 2/2002 | Serhan et al. |
| 2002/0026244 A1 | 2/2002 | Trieu |
| 2002/0032444 A1 | 3/2002 | Mische |
| 2002/0032447 A1 | 3/2002 | Weikel et al. |
| 2002/0038123 A1 | 3/2002 | Visotsky et al. |
| 2002/0052608 A1 | 5/2002 | Kvarnstrom et al. |
| 2002/0055745 A1 | 5/2002 | Mckinley et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072801 A1 | 6/2002 | Michelson |
| 2002/0077632 A1 | 6/2002 | Tsou |
| 2002/0077700 A1 | 6/2002 | Varga et al. |
| 2002/0077702 A1 | 6/2002 | Castro |
| 2002/0082598 A1 | 6/2002 | Teitelbaum |
| 2002/0082693 A1 | 6/2002 | Ahlgren |
| 2002/0082699 A1 | 6/2002 | Ward et al. |
| 2002/0087163 A1 | 7/2002 | Dixon et al. |

(56) References Cited

U.S. PATENT DOCUMENTS

| | | |
|---|---|---|
| 2002/0095154 A1 | 7/2002 | Atkinson et al. |
| 2002/0099384 A1 | 7/2002 | Scribner et al. |
| 2002/0107573 A1 | 8/2002 | Steinberg |
| 2002/0110439 A1 | 8/2002 | Craven |
| 2002/0123807 A1 | 9/2002 | Cauthen, III |
| 2002/0128714 A1 | 9/2002 | Manasas et al. |
| 2002/0147485 A1 | 10/2002 | Mamo et al. |
| 2002/0147496 A1 | 10/2002 | Belef et al. |
| 2002/0147497 A1 | 10/2002 | Belef et al. |
| 2002/0151979 A1 | 10/2002 | Lambrecht et al. |
| 2002/0151980 A1 | 10/2002 | Cauthen, III |
| 2002/0156528 A1 | 10/2002 | Gau |
| 2002/0156531 A1 | 10/2002 | Felt et al. |
| 2002/0161444 A1* | 10/2002 | Choi ............... A61F 2/446 623/17.11 |
| 2002/0165542 A1 | 11/2002 | Ferree |
| 2002/0165612 A1 | 11/2002 | Gerber et al. |
| 2002/0173851 A1 | 11/2002 | Mckay |
| 2002/0183758 A1 | 12/2002 | Middleton et al. |
| 2002/0183848 A1 | 12/2002 | Ray et al. |
| 2002/0188292 A1 | 12/2002 | Sharkey et al. |
| 2002/0188299 A1 | 12/2002 | Reiley et al. |
| 2002/0198599 A1 | 12/2002 | Haldimann |
| 2003/0004574 A1 | 1/2003 | Ferree |
| 2003/0009226 A1 | 1/2003 | Graf |
| 2003/0023311 A1 | 1/2003 | Trieu |
| 2003/0028193 A1 | 2/2003 | Weil et al. |
| 2003/0033017 A1 | 2/2003 | Lotz et al. |
| 2003/0036798 A1 | 2/2003 | Alfaro et al. |
| 2003/0045881 A1 | 3/2003 | Barouk et al. |
| 2003/0065394 A1 | 4/2003 | Michelson |
| 2003/0083668 A1 | 5/2003 | Rogers et al. |
| 2003/0083688 A1 | 5/2003 | Simonson |
| 2003/0130577 A1 | 7/2003 | Purdy et al. |
| 2003/0130664 A1 | 7/2003 | Boucher et al. |
| 2003/0158556 A1 | 8/2003 | Taras et al. |
| 2003/0176926 A1 | 9/2003 | Boehm et al. |
| 2003/0181982 A1 | 9/2003 | Kuslich |
| 2003/0191474 A1 | 10/2003 | Cragg et al. |
| 2003/0195628 A1 | 10/2003 | Bao et al. |
| 2003/0195630 A1 | 10/2003 | Ferree |
| 2003/0204189 A1 | 10/2003 | Cragg |
| 2003/0212400 A1 | 11/2003 | Bloemer et al. |
| 2003/0220643 A1 | 11/2003 | Ferree |
| 2003/0220649 A1 | 11/2003 | Bao et al. |
| 2004/0002708 A1 | 1/2004 | Ritland |
| 2004/0006346 A1 | 1/2004 | Holmen et al. |
| 2004/0010317 A1 | 1/2004 | Lambrecht et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0044412 A1 | 3/2004 | Lambrecht et al. |
| 2004/0059339 A1 | 3/2004 | Roehm et al. |
| 2004/0064143 A1 | 4/2004 | Hicken et al. |
| 2004/0097924 A1 | 5/2004 | Lambrecht et al. |
| 2004/0138752 A1 | 7/2004 | Michelson |
| 2004/0141827 A1 | 7/2004 | Dicke |
| 2004/0151559 A1 | 8/2004 | Craven |
| 2004/0193155 A1 | 9/2004 | Castaneda |
| 2004/0230195 A1 | 11/2004 | Kaikkonen et al. |
| 2004/0236431 A1 | 11/2004 | Sekel |
| 2004/0267269 A1 | 12/2004 | Middleton et al. |
| 2005/0004593 A1 | 1/2005 | Simonson |
| 2005/0010297 A1 | 1/2005 | Watson et al. |
| 2005/0027358 A1 | 2/2005 | Suddaby |
| 2005/0038438 A1 | 2/2005 | Anderson et al. |
| 2005/0101961 A1 | 5/2005 | Huebner et al. |
| 2005/0107791 A1 | 5/2005 | Manderson |
| 2005/0113836 A1 | 5/2005 | Lozier et al. |
| 2005/0113919 A1 | 5/2005 | Cragg et al. |
| 2005/0137604 A1 | 6/2005 | Assell et al. |
| 2005/0137607 A1 | 6/2005 | Assell et al. |
| 2005/0149049 A1 | 7/2005 | Assell et al. |
| 2005/0149191 A1 | 7/2005 | Cragg et al. |
| 2005/0177117 A1 | 8/2005 | Crocker et al. |
| 2005/0228420 A1 | 10/2005 | Harding et al. |
| 2005/0257660 A1 | 11/2005 | Hayden |
| 2005/0261695 A1 | 11/2005 | Cragg et al. |
| 2005/0277847 A1 | 12/2005 | Belinson |
| 2006/0058800 A1* | 3/2006 | Ainsworth ............ A61B 17/70 606/86 A |
| 2006/0155297 A1 | 7/2006 | Ainsworth et al. |
| 2006/0206208 A1 | 9/2006 | Michelson |
| 2006/0206209 A1 | 9/2006 | Cragg et al. |
| 2006/0229622 A1 | 10/2006 | Huebner et al. |
| 2006/0264957 A1 | 11/2006 | Cragg et al. |
| 2007/0010819 A1 | 1/2007 | Johnstone |
| 2007/0016241 A1 | 1/2007 | von Oepen et al. |
| 2007/0066977 A1 | 3/2007 | Assell et al. |
| 2007/0093847 A1 | 4/2007 | Scribner et al. |
| 2007/0112351 A1 | 5/2007 | Assell et al. |
| 2007/0118132 A1 | 5/2007 | Culbert et al. |
| 2007/0167951 A1 | 7/2007 | Ainsworth et al. |
| 2007/0168036 A1 | 7/2007 | Ainsworth et al. |
| 2007/0260270 A1 | 11/2007 | Assell et al. |
| 2008/0004707 A1 | 1/2008 | Cragg |
| 2008/0033466 A1 | 2/2008 | Assell et al. |
| 2008/0065076 A1 | 3/2008 | Cragg |
| 2008/0065080 A1 | 3/2008 | Assell et al. |
| 2008/0065092 A1 | 3/2008 | Assell et al. |
| 2008/0071278 A1 | 3/2008 | Assell et al. |
| 2008/0097452 A1 | 4/2008 | Assell et al. |
| 2008/0154275 A1 | 6/2008 | Assell et al. |
| 2008/0188895 A1 | 8/2008 | Cragg |
| 2008/0195156 A1 | 8/2008 | Ainsworth et al. |
| 2008/0262502 A1 | 10/2008 | Ainsworth et al. |
| 2008/0262555 A1 | 10/2008 | Assell |
| 2009/0105768 A1 | 4/2009 | Cragg et al. |
| 2009/0240293 A1 | 9/2009 | Cragg |
| 2009/0240335 A1 | 9/2009 | Arcenio et al. |
| 2009/0270902 A1 | 10/2009 | Assell et al. |
| 2009/0292287 A1 | 11/2009 | Cragg et al. |
| 2010/0004690 A1 | 1/2010 | Cragg et al. |
| 2010/0137991 A1 | 6/2010 | Ainsworth |
| 2010/0145462 A1 | 6/2010 | Ainsworth |
| 2010/0161057 A1* | 6/2010 | Berry ............... A61F 2/447 623/17.16 |
| 2011/0029019 A1 | 2/2011 | Ainsworth et al. |
| 2011/0035005 A1 | 2/2011 | Ainsworth et al. |
| 2011/0040329 A1 | 2/2011 | Ainsworth |
| 2011/0082424 A1 | 4/2011 | Barnhouse |
| 2011/0112373 A1 | 5/2011 | Ainsworth et al. |
| 2011/0184420 A1 | 7/2011 | Barnhouse |
| 2011/0270312 A1 | 11/2011 | Assell et al. |
| 2011/0282396 A1* | 11/2011 | Shimko ............ A61C 8/0074 606/303 |
| 2012/0123543 A1 | 5/2012 | Cragg |
| 2013/0018473 A1 | 1/2013 | Cragg |

FOREIGN PATENT DOCUMENTS

| | | |
|---|---|---|
| EP | 0334116 | 9/1989 |
| EP | 0611116 | 4/1994 |
| EP | 0807415 | 11/1997 |
| EP | 0890341 | 1/1999 |
| EP | 0980677 | 2/2000 |
| EP | 1029519 | 8/2000 |
| EP | 1283026 | 2/2003 |
| JP | 11-502437 | 3/1999 |
| JP | 2003-102741 | 4/2003 |
| WO | WO 95/22285 | 8/1995 |
| WO | WO 96/11639 | 4/1996 |
| WO | WO 96/28118 | 9/1996 |
| WO | WO 97/31577 | 9/1997 |
| WO | WO 97/40878 | 11/1997 |
| WO | WO 98/02201 | 1/1998 |
| WO | WO 98/17190 | 4/1998 |
| WO | WO 98/38918 | 9/1998 |
| WO | WO 98/49945 | 11/1998 |
| WO | WO 99/39724 | 8/1999 |
| WO | WO 99/47055 | 9/1999 |
| WO | WO 99/51149 | 10/1999 |
| WO | WO 00/53077 | 9/2000 |
| WO | WO 00/67650 | 11/2000 |

(56) References Cited

FOREIGN PATENT DOCUMENTS

| WO | WO 01/28468 | 4/2001 |
|---|---|---|
| WO | WO 01/60234 | 8/2001 |
| WO | WO 01/60263 | 8/2001 |
| WO | WO 01/60268 | 8/2001 |
| WO | WO 02/09801 | 2/2002 |
| WO | WO 02/13732 | 2/2002 |
| WO | WO 02/17825 | 3/2002 |
| WO | WO 02/34120 | 5/2002 |
| WO | WO 02/058599 | 8/2002 |
| WO | WO 02/071921 | 9/2002 |

OTHER PUBLICATIONS

A. Schreiber, and Leu, Hj., "Percutaneous Nucleotomy: Technique with Discoscopy," Orthopedics, Apr. 1991, vol. 14, No. 4, pp. 439-446.

A. Schreiber et al. "Does Percutaneous Nucleotomy With Discoscopy Replace Conventional Discectomy?," Clinical Orthopaedics and Related Research, No. 238, Jan. 1989, pp. 35-42.

B. Jeanneret, et al., "Posterior Stabilization in L5-S1 Isthmic Spondylolisthesis with Paralaminar Screw Fixation: Anatomical and Clinical Results," Journal of Spinal Disorders, vol. 9, No. 3, pp. 223-233 (1996) Lippincott-Raven Publishers, Philadelphia.

C. Dickman, M.D., et al., "Transpedicular screw-rod fixation of the lumbar spine: operative technique and outcome in 104 cases," J. Neurosurg, Dec. 1992, vol. 77, pp. 860-870.

F. Rathke and Karl F. Schlegel, Surgery of the Spine, Atlas of Orthopaedic Operations, vol. 1, 1979, pp. 222-224.

H. Mathews, M.D., "Minimally Invasive Fusion Techniques, Percutaneous Interbody Fusions," Orthopedic Clinics of North America, Oct. 1998, vol. 29, No. 4.

H. Mathews, M.D., et al., "Perspectives on Modern Orthopaedics, Minimally Invasive Techniques for the Treatment of Intervertebral Disk Herniation," Journal of the American Academy of Orthopaedic Surgeons, Mar./Apr. 2002, vol. 10, No. 2.

J. Dove, FRCS, "The Hartshill System for the Front of the Lumbosacral Spine," Lumbosacral and Spinopelvic Fusion, Chapter 42 (pp. 539-543) Lippincott-Raven Publishers (1996).

J. Trambert, M.D., "Percutaneous Interventions in the Presacral Space: CT-guided Precoccygeal Approach—Early Experience," (Radiology 1999; 213:901-904).

J. Olgilvie, M.D., et al., "Overview of Fixation to the Sacrum & Pelvis in Spinal Surgery," Lumbosacral and Spinopelvic Fusion, Chapter 17 (pp. 191-198) Lippincott-Raven Publishers (1996).

J. Smith, MD, et al., "Clinical Outcome of Trans-Sacral Interbody Fusion After Partial Reduction for High-Grade L5-S1 Spondylolisthesis," Spine, 2001, vol. 26, No. 20, pp. 2227-2234.

J. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

M. Gagner et al., Endoscopic Perineal Approach to the Presacral Space: A Feasibility Study, Springer Science + Business Media, LLC Published Jun. 14, 2008 Surg Endosc (2008) 22: 1987-1991 in 5 pages.

M. Macmillan, et al., Biomechanical Analysis of a New Anterior Spine Implant for Post-Corpectomy Instability, Journal of Spinal Disorders, 1995, vol. 8, No. 1, pp. 56-61.

M. Macmillan, MD, et al., "Percutaneous Lumbosacral Fixation and Fusion," Percutaneous Spine Techniques, Jan. 1996, vol. 7, No. 1, pp. 99-106.

M. Zindrick, M.D., et al., "Clinical Anatomy of the Lumbosacral Junction and Pelvix," Lumbosacral and Spinopelvic Fusion, Chapter 2 (pp. 13-25) Lippincott-Raven Publishers (1996).

P. Kambin, M.D., et al., "Arthroscopic fusion of the Lumbosacral Spine," Lumbosacral and Spinopelvic Fusion, Chapter 44 (pp. 565-577) Lippincott-Raven Publishers (1996).

P. Kambin, M.D., et al., "Arthroscopic Discectomy of the Lumbar Spine," Clinical Orthopaedics and Related Research, Apr. 1997, No. 337.

P. Kambin, M.D., et al., "Arthroscopic Microdiscectomy: An Alternative to Open Disc Surgery," The Mount Sinai Journal of Medicine, Sep. 2000, vol. 67, No. 4.

R. Johnsson, et al., "Posterolateral Lumbar Fusion Using Facet Joint Fixation With Biodegradable Rods: A Pilot Study," Eur Spine J., (1997) 6:144-148.

R. Louis, M.D., "Anatomy, Physiology, and Biomechanics of the Lumbopelvic Junction," Lumbosacral and Spinopelvic Fusion, Chapter 1 (pp. 1-11) Lippincott-Raven Publishers (1996).

R. Louis, M.D., "Lumbopelvic Fusion," Lumbosacral and Spinopelvic Fusion, Chapter 38, (pp. 479-492) Lippincott-Raven Publishers (1996).

R. Slone, MD, et al., "Spinal Fixation, Part 1, Basic Hardware, and Fixation Techniques for the Cervical Spine," RadioGraphics, 1993, vol. 13, No. 2, pp. 341-356.

R. Slone, MD, et al., "Spinal Fixation, Part 2, Fixation Techniques and Hardware for the Thoracic and Lumbosacral Spine," RadioGraphics, 1993, vol. 13, No. 3, pp. 521-543.

S. Caruso, M.E., et al., "Instrumented Fusions of the Lumbosacral Spine: A Technical Overview," Lumbosacral and Spinopelvic Fusion, Chapter 18 (pp. 199-210) Lippincott-Raven Publishers (1996).

\* cited by examiner

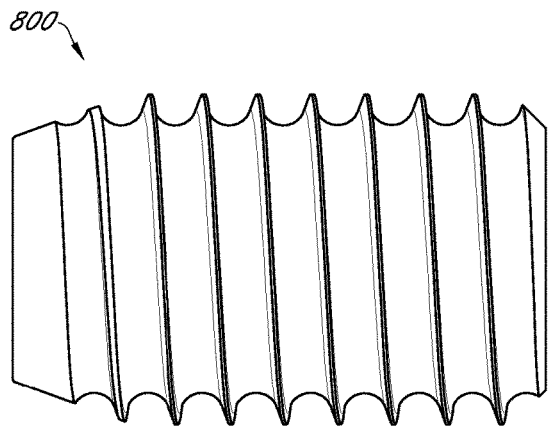 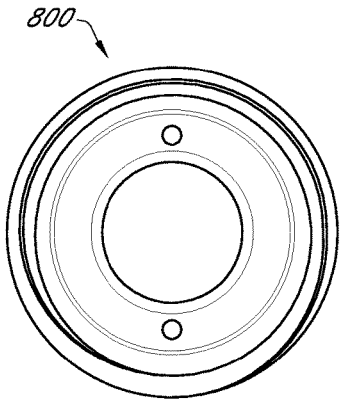
FIG. 14A  FIG. 14B
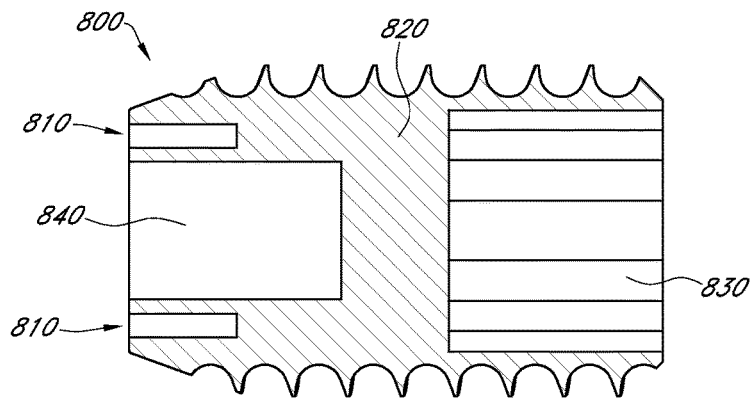
FIG. 14C
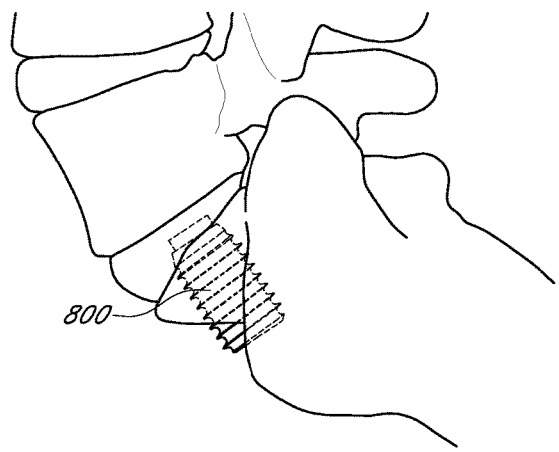
FIG. 14D

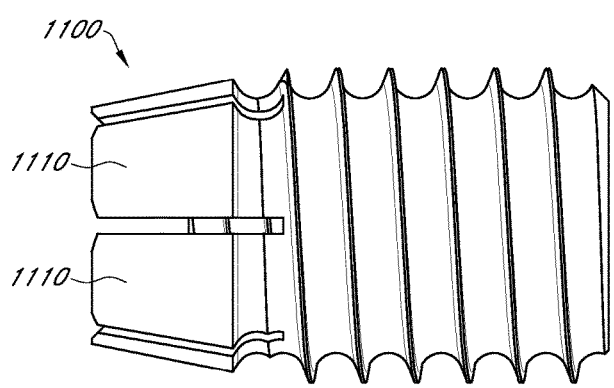
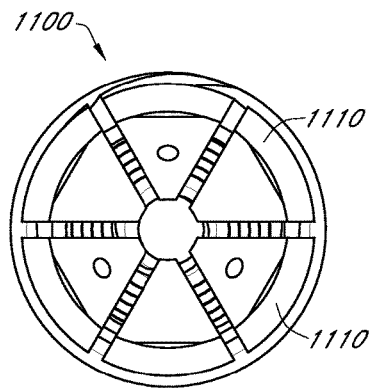
FIG. 17A    FIG. 17B
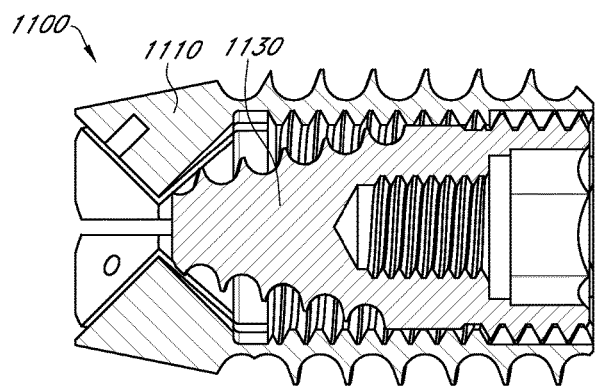
FIG. 17C
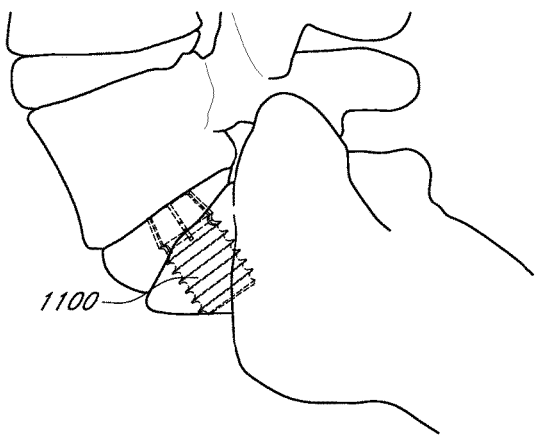
FIG. 17D

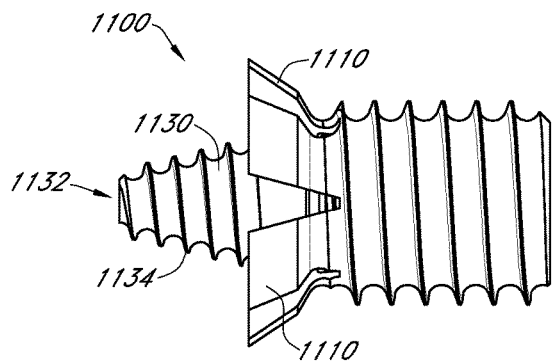
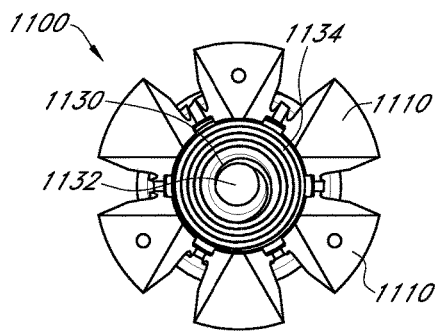
FIG. 17E  FIG. 17F
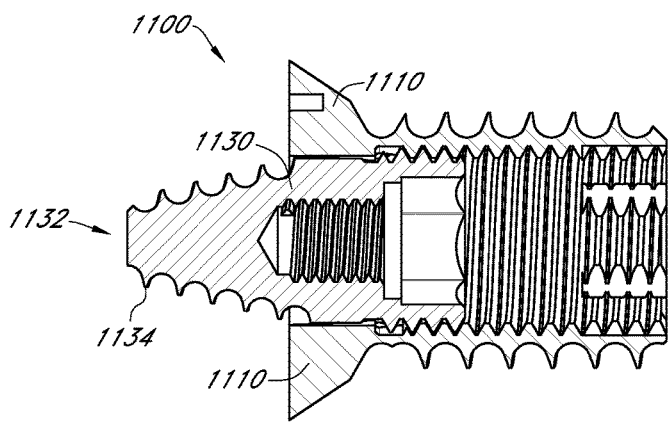
FIG. 17G
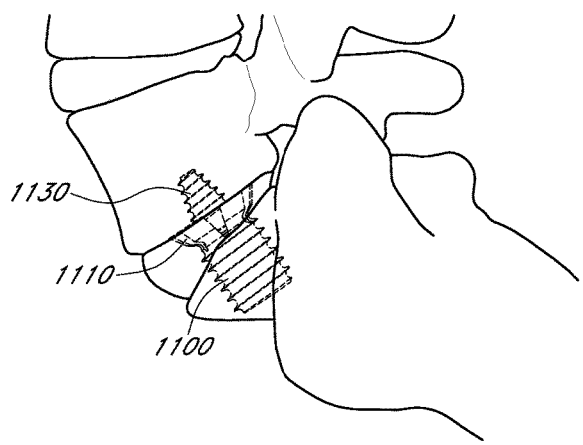
FIG. 17H

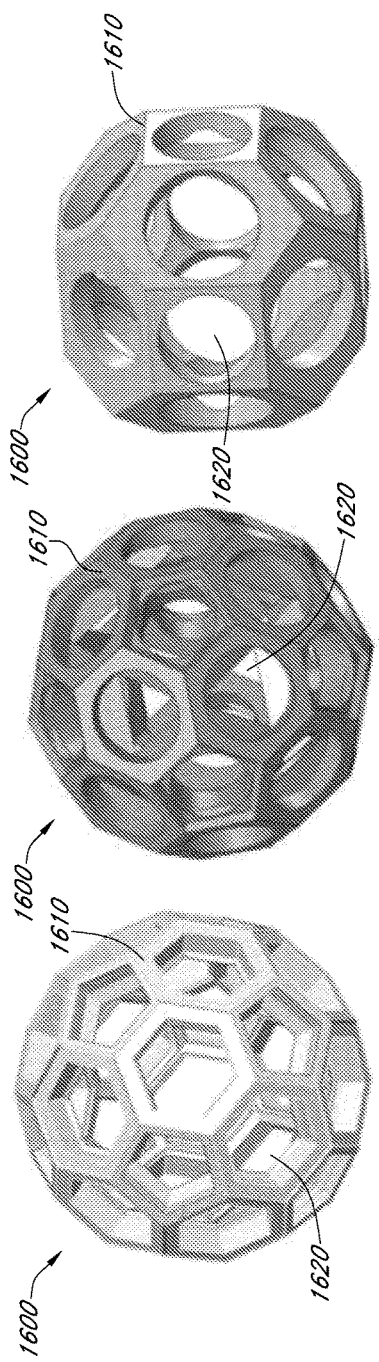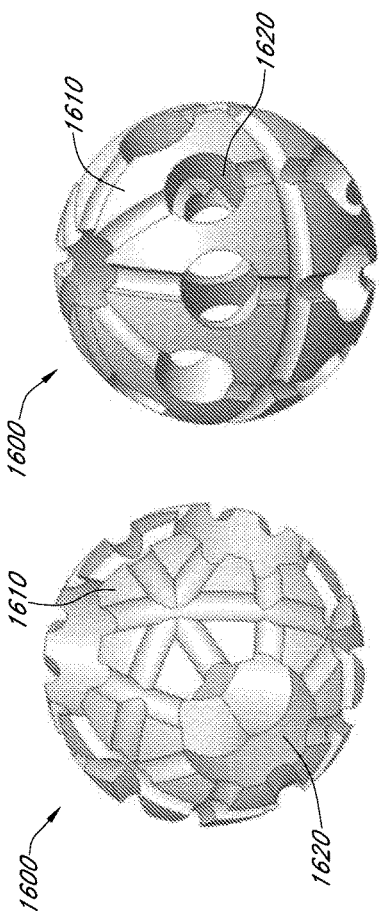
FIG. 22C
FIG. 22B
FIG. 22A
FIG. 23B
FIG. 23A

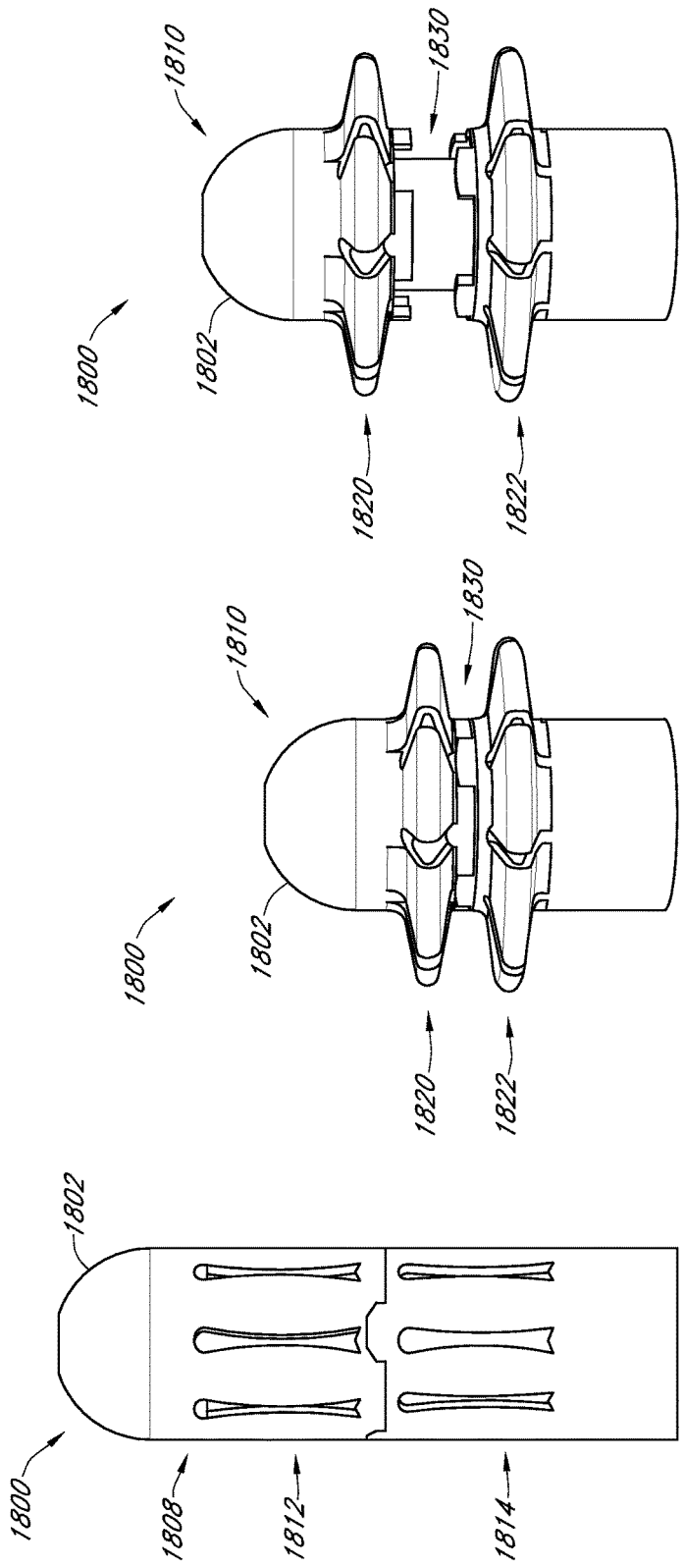

US 9,814,598 B2

SPINAL IMPLANTS AND IMPLANTATION SYSTEM

INCORPORATION BY REFERENCE TO ANY PRIORITY APPLICATIONS

This application claims the benefit of U.S. Provisional App. 61/851,976, filed Mar. 14, 2013, which is incorporated by reference in its entirety herein. Any and all applications for which a foreign or domestic priority claim is identified in the Application Data Sheet as filed with the present application are hereby incorporated by reference under 37 CFR 1.57.

FIELD OF THE DISCLOSURE

The present invention relates to medical devices, systems and methods used in minimally invasive spinal surgery. More particularly, this invention is directed to spinal stabilization and arthrodesis by implantation of devices via a pre-sacral approach.

BACKGROUND

The present disclosure is an extension of work assigned to Quandary Medical LLC, with a principle place of business located in Denver, CO. Much of the access work is described in great detail in the many commonly-assigned applications including U.S. Pat. No. 7,530,993 which describes surgical tools, tool sets and methods for percutaneously accessing and preparing treatment sites on the sacrum of the spine. As described in the present disclosure and application, after the spine is accessed, various devices and tools can be inserted into the spine trans-sacrally in order to treat various spinal disorders and injuries. Examples of such procedures and associated devices and tools are disclosed in additional applications including U.S. Provisional Patent Application No. 60/182,748, filed Feb. 16, 2000, U.S. patent application Ser. No. 09/640,222, filed on Aug. 16, 2000 now U.S. Pat. No. 6,575,979, U.S. patent application Ser. No. 09/782,583 filed on Feb. 13, 2001, now U.S. Pat. No. 6,558,390, U.S. patent application Ser. No. 09/848,556 filed on May 3, 2001, now U.S. Pat. No. 7,014,633, U.S. patent application Ser. No. 10/125,771 filed on Apr. 18, 2002, now U.S. Pat. No. 6,899,716, U.S. patent application Ser. No. 10/309,416 filed on Dec. 3, 2002, now U.S. Pat. No. 6,921,403, U.S. patent application Ser. No. 10/972,065, filed on Oct. 22, 2004, U.S. patent application Ser. No. 11/189,943 filed Jul. 26, 2005, now U.S. Pat. No. 7,608,077, and U.S. patent application Ser. No. 11/501,351, filed on Aug. 9, 2006, U.S. Provisional Application No. 61/259,977 filed on Nov. 10, 2009 and U.S. patent application Ser. No. 12/916,463 filed Oct. 29, 2010, the contents of each of which are incorporated in their entirety into this disclosure by reference herein.

The trans-sacral approach to lumbar surgery described in the above-referenced patents and patent applications represents a pioneering and innovative approach to spinal surgery. In addition, the surgical tools and methods described in these references provide for a minimally invasive and reproducible approach for providing access to primarily, but not limited to, the L4-L5 and L5-S1 vertebral bodies. The devices and methods described above are commercially available and are made by Quandary Medical LLC, and sold under the trademark AXIALIF®. Accordingly, the background of the disclosure provided herein does not repeat all of the detail provided in the earlier applications, but instead highlights how the present disclosure adds to this body of work. Moreover, as with any implants, surgical tools and methods, there remains a need to continuingly improve such implants, tools and methods.

The spine is formed of a series of bones called vertebrae. A vertebra consists of two essential parts including an anterior segment or body, and a posterior part, or vertebral or neural arch. These two parts enclose the vertebral foramen, which together form a canal for the protection of the spinal cord. The vertebral arch consists of a pair of pedicles and a pair of laminae. The body is the largest part of a vertebra, and is generally cylindrical with flattened upper and lower surfaces. The pedicles are two short, thick processes, which project backward, one on either side, from the upper part of the body, at the junction of its posterior and lateral surfaces.

FIG. 1 shows the various segments of a human spinal column as viewed from the side. Each pair of adjacent vertebral bodies and the intervertebral space contributes to the overall flexibility of the spine (known as a motion segment) and contributes to the overall ability of the spine to flex to provide support for the movement of the trunk and head. The vertebrae of the spinal cord are conventionally subdivided into several sections. Moving from the head to the tailbone, the sections are cervical 104, thoracic 108, lumbar 112, sacral 116, and coccygeal 120. The individual segments within the sections are identified by number starting at the vertebral body closest to the head. Of particular interest in this application are the vertebral bodies in the lumbar section and the sacral section. As the various vertebral bodies in the sacral section are usually (naturally) fused together in adults, it is sufficient and perhaps more descriptive to merely refer to the sacrum rather than the individual sacral components.

The individual motion segments within the spinal columns allow movement within constrained limits and provide protection for the spinal cord. The discs are important to allow the spinal column to be flexible and to bear the large forces that pass through the spinal column as a person walks, bends, lifts, or otherwise moves. Unfortunately, for a number of reasons noted below, for some people one or more discs in the spinal column will not operate as intended. The reasons for disc problems range from a congenital defect, disease, injury, or degeneration attributable to aging. Often when the discs are not operating properly, the gap between adjacent vertebral bodies is reduced and this causes additional problems including pain.

Instability of spinal joints may result from, for example, trauma (to ligamentous structures; fracture, or dislocation); degenerative disease processes (e.g., rheumatoid arthritis; degenerative spondylosis; spondylolisthesis; spinal stenosis); tumor; infection, or congenital malformation that may lead to significant pathological translation, or longitudinal displacement. Cord compression and trauma to the spinal cord can result in respiratory distress, pain, nerve dysfunction, paresis and paralysis, or even sudden death. Therefore, the need for spinal stabilization in the setting of pathological instability is paramount.

Spinal arthrodesis, or fusion, provides needed biomechanical stability and is a therapy used to treat such instability. The objective is to create a stable biomechanical environment and provide the biological requirements for osseous fusion. Adequate decompression of the neurological structures, where indicated, and recreation of normal sagittal and coronal alignment are prerequisites prior to an arthrodesis procedure. Spinal fixation has been achieved using a variety of techniques to provide stabilization and/or spinal alignment, followed by fusion, or arthrodesis by means of bone graft insertion. Over the years, various techniques and systems have been developed for correcting spinal injuries and/or degenerative spinal processes. One class of solutions is to remove the failed disc and then fuse the two adjacent vertebral bodies together with a permanent but inflexible spacing, also referred to as static stabilization. Fusing one section together ends the ability to flex in that motion segment. However, as each motion segment only contributes a small portion of the overall flexibility of the spine, it can be a reasonable trade-off to give up the flexibility of a motion segment in an effort to alleviate significant back pain.

Thus, spinal correction frequently requires stabilizing a portion of the spine to facilitate fusing portions of the spine or other correction methodologies and medical correction of this type is frequently employed for many spinal conditions, such as, for example, degenerative disc disease, scoliosis, spinal stenosis, or the like. Frequently, these corrections also require the use of implants and/or bone grafts. Stabilizing the spine allows bone growth between vertebral bodies such that a portion of the spine is fused into a solitary unit.

Among techniques and systems that have been developed for correcting and stabilizing the spine and facilitating fusion at various levels of the spine is a system for axial trans-sacral access. One example of axial trans-sacral access to the lumbo-sacral spine as shown in FIGS. 2A and 2B below, reduces the need for muscular dissection and other invasive steps associated with, traditional spinal surgery while allowing for the design and deployment of new and improved instruments and therapeutic interventions, including stabilization, mobility preservation, and fixation devices/fusion systems across a progression-of-treatment in intervention. FIGS. 2A and 2B show an example of a process of "walking" a blunt tip stylet 204 up the anterior face of the sacrum 116 to the desired position on the sacrum 116 while monitored on a fluoroscope (not shown). This process moves the rectum 208 out of the way so that a straight path is established for the subsequent steps. FIG. 2C illustrates a representative axial trans-sacral channel 212 established through the sacrum 116, the L5/sacrum intervertebral space, the L5 vertebra 216, the L4/L5 intervertebral space, and into the L4 vertebra 220.

The use of a trans-sacral approach to provide spinal therapy is described in co-pending and commonly assigned U.S. Pat. Nos. 6,921,403, 7,588,574 and which are incorporated by reference into this application. A brief overview of this method of accessing the spinal region to receive therapy is useful to provide context for the present disclosure. As shown in FIG. 2A, a pre-sacral approach through percutaneous anterior track towards sacral target, through which trans-sacral axial bore will be made and the access channel extended distally for subsequent advancement of multi-level axial spinal stabilization assemblies. An anterior, pre-sacral, percutaneous tract extends through the pre-sacral space anterior to the sacrum. The pre-sacral, percutaneous tract is preferably used to introduce instrumentation to access and prepare the access channel (e.g., by drilling a bore in the distal/cephalad direction through one or more lumbar vertebral bodies and intervening discs). "Percutaneous" in this context simply means through the skin and to the posterior or anterior target point, as in transcutaneous or transdermal, without implying any particular procedure from other medical arts. However, percutaneous is distinct from a surgical access, and the percutaneous opening in the skin is preferably minimized so that it is less than 4 cm across, preferably less than 2 cm, and, in certain applications, less than 1 cm across. The percutaneous pathway is generally axially aligned with the bore extending from the respective anterior or posterior target point through at least one sacral vertebral body and one or more lumbar vertebral body in the cephalad direction as visualized by radiographic or fluoroscopic equipment.

More specifically, as shown in FIG. 2B, the lumbar spine is accessed via a small skin puncture adjacent to the tip of the coccyx bone. The pre-sacral space is entered, using standard percutaneous technique, and the introducer assembly with the stylet's blunt tip serving as a dilator is placed through the paracoccygeal entry site. Once the tip of the stylet is through the facial layer, the blunt tip is rotated back against the anterior face of the sacrum and "walked" to the desired position on the sacrum under fluoroscopic guidance. Once the target site has been accessed and risk of soft tissue damage mitigated, the blunt-tipped stylet is removed and a guide pin, or wire, is safely introduced through the guide pin introducer tube, and "tapped in". The guide pin establishes the trajectory for placement of subsequent bone dilators and sheath through which a twist drill is introduced creating an axial bore track, the lumen of which is extended distally. The guide pin maintains the axial alignment of access and preparation tools as well as the alignment of cannulated spinal stabilization devices and assemblies, of larger diameter than the bore track, that are subsequently introduced over a 23" long, 0.090" diameter guide pin and through an exchange cannula for deployment within the vertebral column, as described at least in part in co-pending and commonly assigned U.S. patent application Ser. Nos. 10/972,065, 10/971,779, 10/971,781, 10/971,731, 10/972,077, 10/971,765, 10/971,775, 10/972,299, and 10/971,780, all of which were filed on Oct. 22, 2004, and in co-pending and commonly assigned United States Provisional Patent Application "Method and Apparatus for Access and Deployment of Spinal Stabilization Devices Through Tissue", 60/706,704 filed Aug. 9, 2005, and Exchange System For Axial Spinal Procedures Ser. No. 11/501,351 filed Aug. 9, 2006, and all of which are incorporated by reference herein in their entirety.

U.S. patent application Ser. No. 12/916,463, which is hereby incorporated by reference in its entirety, discloses additional methods, techniques and devices for providing a trans-sacral approach to provide spinal therapy. For example, the tissue retraction device (not shown)) can be inflated or otherwise expanded to device a working space or channel that is generally positioned between the bowl and the sacrum. The working space or channel created by the tissue retraction device can form a portal that extends from a target site on a patient's sacrum towards or to a surgical access site such that tools and instruments can be inserted from the surgical access site, through the portal and to the target site. In these examples, the tissue retraction device can serve to protect the patient's soft tissue (e.g., the bowel) as the instruments are advanced towards the target site on the sacrum. In certain examples, the tissue retraction device can provide substantially 360 degrees (about the longitudinal axis of the device) of protection about the portal. In this manner, as tools are advanced towards the access site the tissue retraction device completely surrounds such tools preventing the tools from contacting or traumatizing the soft tissues of the patient. In other examples, the tissue retraction device can form an atraumatic barrier between the tools and the bowel as tools are passed over or partially through the device. In certain examples, the tissue retraction device can also retract the bowel from the sacrum and/or dissect tissue. An advantage of certain examples is that the tissue retractor can conform to the face of the sacrum.

While stabilization procedures, and in particular surgical implants, instrumentation, and techniques, continue to evolve in the pursuit of improvements in clinical outcomes (e.g., the highest fusion rate with the shortest time to fusion and improvement in neurological function), and in simplicity of use, notwithstanding, there remains a need for ongoing advancements in spinal implant constructs and systems leading to progress in the surgical management of complex spinal disorders, to accommodate an increased spectrum of anatomical variations, to enable simplicity of instrumentation placement, and to avoid certain adverse events such as loss of spinal alignment, in order to achieve more rigid stabilization in a wider variety of spinal diseases.

There are disclosed herein surgical implants, instruments and methods for minimally invasive spinal stabilization or fusion. It is believed that the use of the systems disclosed herein will overcome limitations noted above and will result in improved maintenance of alignment, increased rate of successful arthrodesis, and minimized occurrence of adverse events as evidenced by clinical and radiographic outcomes.

General Comments and Terminology

In the context of the present disclosure, as used herein the terms "assembly" or "constructs" are sometimes used interchangeably and refer to implants, implant systems, instruments, or instruments systems which are configured to comprise multiple components, which may or may not be contiguous. It is further understood that individual components may themselves be configured as sub-assemblies, e.g., comprising a plurality of component materials, and that the formation of the components may involve intermediate processes or appliances. It is further understood that the terms spinal implants, implants, devices, cages, mini-cages, pre-sacral mini-cages and/or spacers are sometimes used interchangeably, and moreover, that "pre-sacral" refers to the fact that the devices are advanced through the pre-sacral space to subsequently access (e.g., by means of trans-sacral insertion) and be deployed into or at an intended target site for therapy, e.g., in a motion segment vertebral body or disc space.

It will also be understood that upon formation of assemblies from multiple components and deployment, individual components of the present disclosure may or may not remain as discernibly distinct. It will also be understood that, for convenience, system components may be packaged and provided either individually, or as in "kits," and either as reusable or disposable.

As used herein, the term "biocompatible" refers to an absence of chronic inflammation response or cytotoxicity when or if physiological tissues are in contact with, or exposed to (e.g., wear debris) the materials and devices of the present disclosure. In addition to biocompatibility, in another aspect of the present disclosure it is preferred that the materials comprising the implant and instrument systems are sterilizable.

In one aspect of the present disclosure, certain components of the device assemblies and systems of the present disclosure are configured to comprise biocompatible materials and are able to withstand, without wear, multiple cycles/procedures without failing. For example, materials selected may include but are not limited to, biomedical titanium, cobalt-chromium, or medical grade stainless steel alloys.

It will be further understood that the length and dimensions of implant components and instruments described herein will depend in part on the target site selection of the treatment procedure and the physical characteristics of the patient, as well as the construction materials and intended functionality, as will be apparent to those of skill in the art.

In order to make it easier for a reader to find certain sections of this document that are of particular interest to the reader, a series of headings have been used. These headings are solely for the purpose of helping readers navigate the document and do not serve to limit the relevance of any particular section exclusively to the topic listed in the heading.

In the context of this discussion: anterior refers to "in front" of the spinal column; (ventral) and posterior refers to "behind" the column (dorsal); cephalad means towards the patient's head; caudal refers to the direction or location that is closer to the feet. Proximal is closer to the surgeon; distal is in use more distant from the surgeon. "Superior" refers to a top or front surface, while "inferior" refers to a back or bottom surface of a device. When referencing tools, distal would be the end intended for insertion into the patient and proximal refers to the other end, generally the end closer to, e.g., a handle for the tool and the user.

The sequence of operations (or steps) is not limited to the order presented in the claims or figures unless specifically indicated otherwise.

SUMMARY

Many variations of spinal implants exist on the market today. However, prior systems are limited in the way of minimally invasive placement of implant systems within the disc space. Accordingly, there is a need for improved systems and methods that permit a combination of axial and lateral or radial deployment of devices into the disc space in a low-trauma manner. As used herein, the terms "laterally" and "radially" are sometimes used interchangeably to describe deployment of the spinal implants of the present disclosure within the disc space.

Currently, using the trans-sacral approaches described above various types of implants can be inserted into the spine. Such implants are sold and made by Quandary Medical LLC, for example, under the trade name "AXI-ALIF® Plus." These implants generally extend across a disc space and into at least two portions of bone superiorly and inferiorly to the disc space. While such implants have been proven to be successful, there is a general need to continue to provide additional implants and techniques that can be used in conjunction with the currently available trans-sacral implants and/or to replace such implants in order to provide improved flexibility, strength and/or stability.

Accordingly, described below are various examples that provide (generally, one or a plurality of) preformed cages, or a system (e.g., of interlocked cages) of cages, spacers, and/or plugs that can be implanted into the L4-S1 disc spaces using a TranS1 presacral approach.

In general, the term cage may refer to an implant or device which facilitates fusion, e.g., by means of incorporation of bone growth media for example in channels in the device which may promote bone in-growth into the device and or between vertebral bodies above and below the disc space into which the implant is inserted. The term spacer may refer to a device or implant, including a cage, whether threaded or unthreaded, which may assist in distracting (increasing the distance therebetween) or supporting the vertebral bodies of a motion segment above and below the disc space into which the spacer is inserted, and which also may correct lordosis (e.g., if wedge shaped). As used herein, the term plug generally refers to a device which fills an access channel through which an implant was introduced, and which precludes migration or egress of a device or of bone growth media back out of the channel. An AXIALIF® implant 100 itself may serve as a plug. As used herein, these terms may sometimes collectively refer to and be used interchangeable with one another with respect to the devices and implants described in the present disclosure The implants as described in the present disclosure may be used as stand-alone devices and/or in conjunction with an AXIALIF® implant 100 and/or with accompanying posterior fixation devices. When used as adjunct implants, these devices are inserted first into the disc space in the sequence of device deployment, e.g., prior to an AXIALIF® implant 100. In certain instances, there may be surgical advantages of use of the presently disclosed implants as stand-alone devices, e.g., without an accompanying AXIALIF® implant 100, e.g., simplicity in terms of fewer steps in deployment. The devices as presently disclosed may also provide added compressive strength to weaker graft material or act as stabilizers to give supplemental stiffness to the construct. In doing so, earlier fusion results may occur more reliably across a larger patient population.

Advantages (vary depending on device design) can include added stabilization; limitation on anterior flexion (or lateral bending/flexion-extension); lordosis correction (e.g., wedge designs) or spondylolisthesis correction; prevent subsidence and transition syndrome.

In accordance with this aspect of the present invention, the devices disclosed herein are believed to prevent the phenomena of subsidence and transition syndrome. As used herein, subsidence refers to the detrimental descent of an orthopedic implant into bone that surrounds it. Transition syndrome refers to altered biomechanics and kinematics of contiguous vertebral levels and concomitant risk of adjacent motion segment instability that may occur as a result of spinal therapeutic procedures that are suboptimal in terms of their ability to restore physiological function and properties, and thus risk a cascading deleterious effect on surrounding otherwise healthy tissue.

Additional advantages and characteristics of certain examples of presently disclosed devices include that they:
  Provide additional anterior support with respect to compressive loading, and stabilization. For example, when used as an adjunct device with an AXIALIF® implant, devices of the present disclosure may limit anterior flexion during bone growth leading to fusion, improving patient outcomes
  House graft/bone growth media
  Exhibit similar compressive stiffness to bone Size range from 4-10 mm in height for varying sized disc spaces
  Are able to be delivered through 12 mm outer diameter (OD; e.g., dilator sheath docked to sacrum) or about 10 mm inner diameter (ID), with a range of up to about 15.5 OD instruments/channel cannulated instruments
  Are able to be delivered through an access channel of about 7 mm
  Have an increased surface area (endplate support footprint) and are able to withstand compressive loads
  Minimize area consumed by the device to allow adequate area for bone to grow; anticipate providing/seeing better radiographic evidence of fusion Yet another advantage of the trans-sacral approach is that the disc annulus is left intact, which aids in device retention and containment once deployed. In some examples, the cages can be held in by friction fit and/or compressive axial loads, e.g., by means of accompanying posterior fixation.

Certain examples of cages/systems, spacers, and plugs may be made of allograft, titanium (or alloys), Nitinol (nickel-titanium alloys that exhibit: shape memory and super-elasticity), or polyether ether ketone (PEEK), or combinations thereof (e.g., for "expandability" of implants) with heights ranging from between about 4 mm (posterior side) to about 10 mm (anterior side) and angles of 0 or for lordotic implants from between about 5 to about 10 degrees to assist in correcting the angle lordosis lost with DDD in the L4-S1 portion of the spine Many of the examples described herein address a design challenge that is involved with trans-sacral access. Specifically, many examples of cage designs can make a 90 degree turn to be placed into the disc space, i.e. progress from axial to lateral deployment, and can include tools for insertion and removal.

As noted above, the device concepts as introduced via the trans-sacral approach (and as described herein are for convenience only sometimes interchangeably referred to as "mini-cages") are spinal implants that may be used in conjunction with AXIALIF® implants 100 (e.g., to achieve improved biomechanical stability with respect to, for example, spondylolisthesis and/or lordosis correction) and/or posterior fixation (e.g., via pedicle screws or facet screws), or as "stand-alone" devices. Certain mini-cage designs (including but not limited to examples as described and shown below) provide anterior support in the form of a cage or scaffold to provide a structure for fusion that can be placed through channel and into disc space to provide structural support as well as a platform or construct for bone to form on for fusion.

Aspects of the teachings contained within this disclosure are addressed in subsequent claims submitted with the Provisional Application upon filing, and/or with its conversion to a formal Patent Application. Rather than adding redundant restatements of the contents of the claims, these claims should be considered incorporated by reference into this summary, although the present disclosure in not intended to be limited in scope by these claims.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The accompanying figures, which are incorporated in and constitute part of this specification, are included to illustrate and provide a further understanding of the system and method of the invention. Together with the description, the figures serve to explain the principles of the invention. Unless indicated, the components in the figures are not necessarily to scale, emphasis instead being placed upon illustrating the principles of the invention. Moreover, in the figures, like referenced features designate corresponding parts throughout the different views.

FIGS. 14A-14D show a 1-piece, non-expanding plug

FIGS. 17A-17H illustrate an example of a threaded cage configured as a flower with petals as above, but the cage is also additionally configured for insertion into an endplate FIGS. 22A-22C and 23A-23B depict spherical "bucky ball" mini-cages FIGS. 25A-25G illustrate examples of winged cages

DETAILED DESCRIPTION

Figure 1:
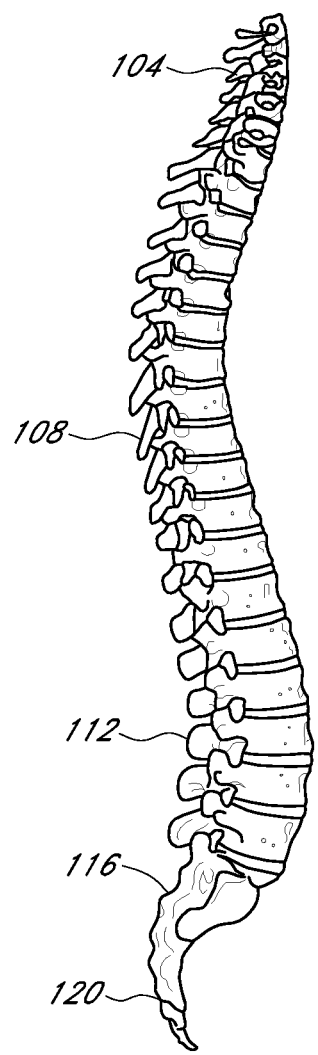
FIG. 1 shows the various segments of a human spinal column as viewed from the side

Described herein are examples directed toward spinal implants/spacers and associated assemblies, especially for application in the spinal stabilization arena. However, as can be appreciated, the associated assemblies disclosed herein can be used in any of a number of clinical applications where insertion of a spinal implant or spacer into or through a vertebral body and/or disc space is desired. The devices, systems, and methods described herein are not intended to limit the scope of this disclosure. Rather, it will be apparent to one of skill in the art that the devices, systems, and methods disclosed herein can be used in varied clinical applications. Additionally, it should be noted that elements of one example can be combined with elements of another example, except where the function of the components prohibits such combinations.

In some examples, a wedge system 400 may be utilized to stabilize the spine. The wedge system 400 is capable of being inserted into a disc space, and maintaining the desired spacing between the surrounding vertebrae. With reference to FIGS. 5-9, one example of a preferred wedge system 400 is illustrated. In one aspect, the wedge system 400 can include a plurality of wedge components (410, 422), a ramped insertion tool 500, and a wedge system cannula (See FIGS. 6A-8). The wedge system 400 can be configured to be implanted into a disc space between two vertebrae with a trans-sacral approach as described above. In one aspect, the wedge system 400 is configured to be implanted into the disc space between the L5 and S1 vertebrae.

FIGS. 6A-6E illustrate the stages of insertion of one example of a wedge system 400 into one example motion segment. As shown, with a trans-sacral approach, an implant delivered to the disc space between the endplate of the upper vertebrae and the endplate of the lower vertebrae must make a sharp turn of approximately 90 degrees in order to move radially outwards from the access/insertion site. In some examples, the wedge system 400 is configured to deliver at least one implant 410 into the disc space with a trans-sacral approach, and then cause the at least one implant 410 to move radially from the implantation site. In some examples, the implants 410 can include a plurality of wedge components 410. In some examples, the plurality of wedge components 410, as illustrated in FIG. 6, are configured to abut the endplate of the upper vertebrae and the endplate of the lower vertebrae, providing a structural support and maintaining a desired vertebral spacing in the disc space between the endplates.

Figure 5:
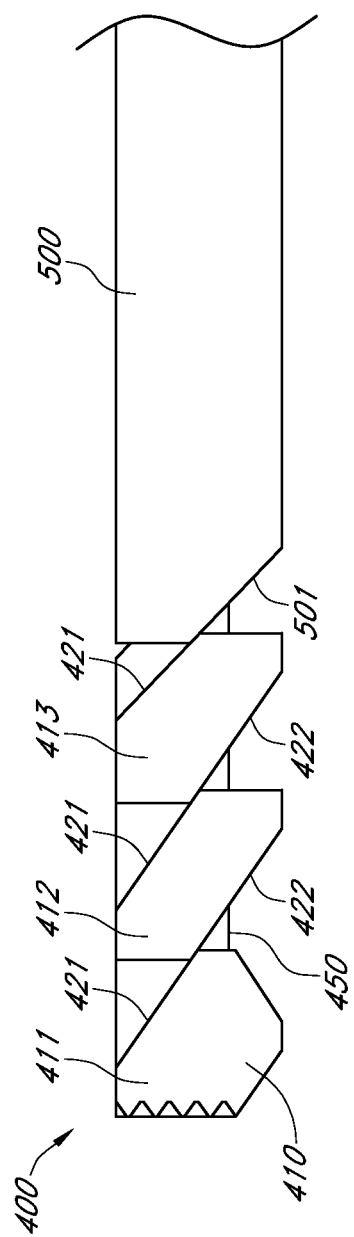
FIG. 5 illustrates a wedge system comprising a plurality of wedge components and a ramped insertion tool

As FIG. 5 illustrates, in some examples a wedge system 400 comprises at least one and often a plurality of wedge components 410 and a ramped insertion tool 500. The plurality of wedge components 410 can include a leading wedge component 411, or a $1^{st}$ wedge component 411 as depicted in FIG. 5, a trailing wedge component 413, or a $3^{rd}$ wedge component 413 as depicted in FIG. 5, and at least one middle wedge component 412, or a $2^{nd}$ wedge component 412 as depicted in FIG. 5. In some examples, as illustrated in FIG. 6, the wedge system 400 can also include a wedge system cannula 510. In some examples, the plurality of wedge components 410 and the ramped insertion tool 500 are constructed to slide within the wedge system cannula 510. In some examples, the wedge system cannula 510 is inserted using a trans-sacral approach, until its upper end is approximately flush with the endplate of the lower vertebrae at the implantation site. In some examples, the wedge system cannula 510 is substantially perpendicular to the endplates. Then, in some examples, the ramped insertion tool 500 can be forced axially through the wedge system cannula 510 towards the disc space between the vertebral endplates forcing the wedge components 410 into the disc space. The plurality of wedge components 410 and ramped insertion tool 500 can be configured such that as they are forced in a first direction 512 along the axis of the wedge system cannula, each successive component in the plurality of components forces the component it is following to change direction and move radially outward from the implantation site in a second direction 513, substantially parallel to the endplates. In some examples, the second direction 513, the direction in which the plurality of wedge components 410 travel radially outward from the access or insertion site, can be dictated by the rotational position of the ramped insertion tool 500 about the axis of the wedge system cannula 510, and thus the plurality of wedge components 410. In some examples, the axial force applied to the ramped insertion tool 500 can be provided by the user, an impact by an additional tool 530 which may include, for example, a slap hammer, or the force could be supplied in a more controlled manner which may include for example, axial motion provided by a threaded portion of the wedge/insertion system.

In some examples, as illustrated in FIG. 5, the $1^{st}$ wedge component 411 can include a first ramped surface 421. The $2^{nd}$ wedge component 412 can include a $2^{nd}$ ramped surface 422. In some examples, the $2^{nd}$ ramped surface 422 of the $2^{nd}$ wedge component 412 is complimentary to the $1^{st}$ ramped surface 421 of the $1^{st}$ wedge component 411. In some examples, as illustrated in FIG. 6, the plurality of wedge components 410 can be configured so that advancement of the $2^{nd}$ wedge component 412 and the $2^{nd}$ ramped surface 422 against the $1^{st}$ wedge component 411 and $1^{st}$ ramped surface 421 in a first direction causes 512 the $1^{st}$ wedge component 411 to move in a second direction 513 that is generally perpendicular to the first direction 512.

In some examples, the wedge insertion system 400 can include a protection tool 525. In some examples, the protection tool 525 can include a substantially flat portion 526 which is configured to abut the endplate of the upper vertebra adjacent the implantation site. The substantially flat portion 526 of the protection tool 525 is configured to prevent the plurality of wedge components 410 from breaking through the endplate of the upper vertebra during insertion. In some examples, the substantially flat portion 526 is made of a material stronger than the endplate of a vertebra.

In some examples, as illustrated in FIG. 5, the 2nd wedge component 412 can include a $1^{st}$ ramped surface 421. The 3rd wedge component 413 can include a 2nd ramped surface 422. In some examples, the 2nd ramped surface 422 of the 3rd wedge component 413 is complimentary to the 1st ramped surface 421 of the 2nd wedge component 412. In some examples, as illustrated in FIGS. 6A-6E, the plurality of wedge components 410 can be configured so that advancement of the 3rd wedge component 413, having a 2nd ramped surface 422 against the 2nd wedge component 412 and its 1st ramped surface 421, in a first direction 512 causes the 2nd wedge component 412 to move in a second direction 513 that is generally perpendicular to the first direction 411. In some examples, the movement of the $2^{nd}$ wedge component 412 in the second direction 513 also causes the $1^{st}$ wedge component 411 to move in the second direction 513.

In some examples, as illustrated in FIG. 5, the wedge system 400 can include a ramped insertion tool 500. In some examples, the ramped insertion tool 500 may include an insertion tool ramped surface 501. In some examples, the $3^{rd}$ wedge component 413 can include a $1^{st}$ ramped surface 421. In some examples, the insertion tool ramped surface 501 of the ramped insertion tool 500 is complementary to the $1^{st}$ ramped surface 421 of the $3^{rd}$ wedge component 413. In some examples, as illustrated in FIGS. 6A-6E, the plurality of wedge components 410 can be configured such that advancement of the ramped insertion tool 500 and the insertion tool ramp surface 501 against the $3^{rd}$ wedge component 413 and $1^{st}$ ramped surface 421 in a first direction causes the $3^{rd}$ wedge component 413 to move in a second direction 513 that is generally perpendicular to the first direction 512. In some examples, the movement of the $3^{rd}$ wedge component 413 in the second direction 513 also causes the $1^{st}$ wedge component 411 and $2^{nd}$ wedge component 412 to move in the second direction 513.

In some examples, the plurality of wedge components 410 can include more than three wedge components 410. In some examples, the plurality of wedge components 410 may include a plurality of middle wedge components 412, or $2^{nd}$ wedge components 412 as depicted in FIG. 5. In some examples, as illustrated in FIGS. 6A-6E, each wedge component 410 can include a top surface 431 and a bottom surface 432. In some examples, the top surface 431 can be configured to abut the endplate of the upper vertebrae. In some examples, the upper vertebra is the L5 vertebrae. In one example, the bottom surface 432 can be configured to abut the endplate of the lower vertebra. In one example, the lower vertebra is the S1 vertebrae. In some examples, the ramped surfaces of each wedge component can be inclined or declined relative to the top surface 431 and/or bottom surface 432. In some examples, the top surface 431 may be substantially perpendicular to the bottom surface 432. In other examples, the top surface 431 may be inclined relative to the bottom surface 432 in order to achieve the desired relationship between the vertebrae above the disc space and the vertebrae below the disc space, e.g., in order to accommodate a lordotic angle between them. In one example, the $1^{st}$ wedge component 411 can include a leading edge upper surface 433 and a leading edge lower surface 434, which converge towards a common point 435. The converging surfaces allow the $1^{st}$ wedge component 411 to self-dilate/distract the disc space to the extent/position desired as it is being advanced radially. In one example, the leading edge upper surface 433 and a leading edge lower surface 434 are configured to aid in the movement of the $1^{st}$ wedge component 411 radially from the implantation site in a second direction 513. In some examples, a leading edge upper surface 433 and a leading edge lower surface 434 are each inclined or declined relative to the top surface 431 or bottom surface 432 of the first wedge component 411.

Figure 8:
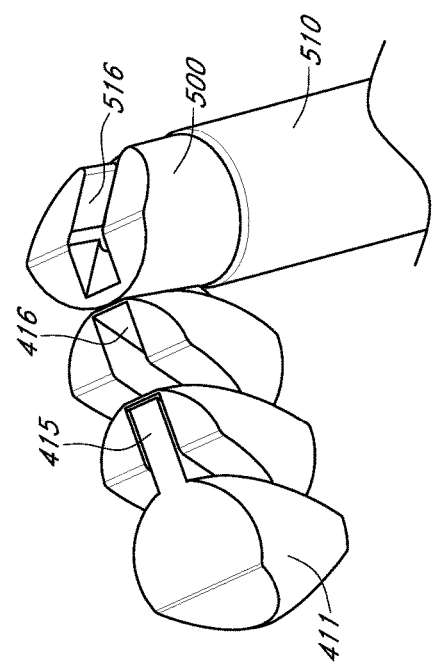
FIG. 8 shows each wedge component can include a wedge protrusion and/or wedge slot where each slot and protrusion are configured to complement one another

In some examples, as illustrated in FIGS. 5 and 8, each wedge component 410 can include a wedge protrusion 415 and/or wedge slot 416 where each slot 416 and protrusion 415 are configured to complement one another. In addition, in some examples, the ramped insertion tool 500 may comprise a tool slot 516 configured to complement a wedge slot 416. In some examples, the wedge protrusions 415 are configured to slide within a wedge slot 416 or tool slot 516, to maintain the radial orientation of the plurality of wedge components 410 during (and after) insertion. In some examples, the wedge protrusion 415 of the $1^{st}$ wedge component 411 is configured to slide within the wedge slot 416 of the $2^{nd}$ wedge component 412. In some examples, the wedge protrusion 415 of the $2^{nd}$ wedge component 412 is configured to slide within the wedge slot 416 of the $3^{rd}$ wedge component 413. In some examples, the wedge protrusion 415 of the $3^{rd}$ wedge component 413 is configured to slide within the tool slot 516 of the ramped insertion tool 500. In some examples, the complementary wedge protrusions 415 and wedge/tool slots (416/516) may include means for retaining the plurality of wedge components 410 together which may include, for example, a dovetail, a key, a metal link, a taper, etc.

Figure 9C:
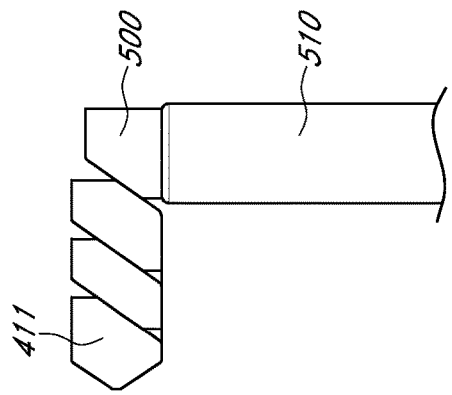
FIGS. 9A-9C illustrate a plurality of wedge components and ramped insertion tool that may be cannulated and configured to receive an insertion rod
Figure 9B:
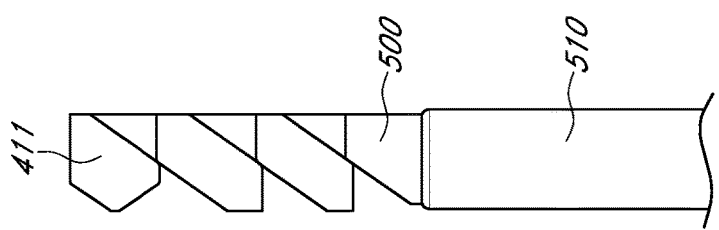
Figure 9A:
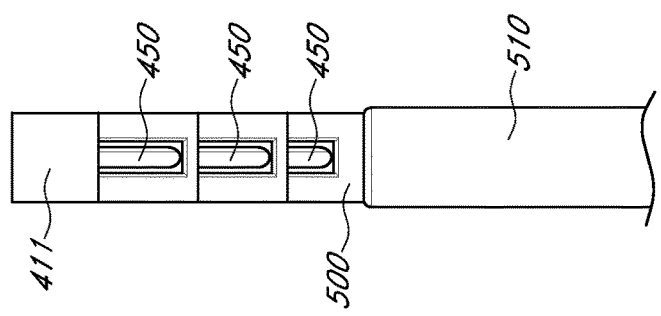

In some examples, as illustrated in FIGS. 9A-C, the plurality of wedge components 410 and ramped retention tool 500 may be cannulated. In some examples, the cannulation can be configured to receive a retention rod 450. In some examples, the wedge system 400 can include an insertion rod 450. The insertion rod 450 can be inserted within the cannulation of the plurality of wedge components 410 and ramped insertion tool 500. In some examples, the insertion rod 450 can be configured (e.g., with protrusions or slots) to maintain the orientation and position of the plurality of wedge components 410 until they are delivered into the disc space. In some examples, the tip of the insertion rod closest to the implantation site can include means for retaining the $1^{st}$ wedge component 411, which may include for example, a friction fit, an external thread configured to complement a corresponding internal thread in the $1^{st}$ wedge component 411, an enlarged portion configured to complement a recess formed within the $1^{st}$ wedge component 411, etc. In some examples, the $1^{st}$ wedge component 411 may include an internal thread configured to complement an external thread of the insertion rod 450. In some examples, the $1^{st}$ wedge component 411 may not be completely cannulated to ensure that the insertion rod 450 does not pass all the way through the $1^{st}$ wedge component 411. In some examples, the means for retaining the first wedge component 411 can be disengaged in order to deliver the plurality of wedge components 410 into the disc space, which may include, for example, rotation of the insertion rod 450, pulling on the insertion rod 450, etc.

Figure 6A:
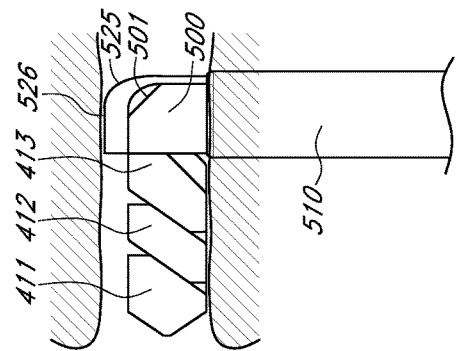
FIGS. 6A-6E illustrate the stages of insertion of one example of a wedge system
Figure 6B:
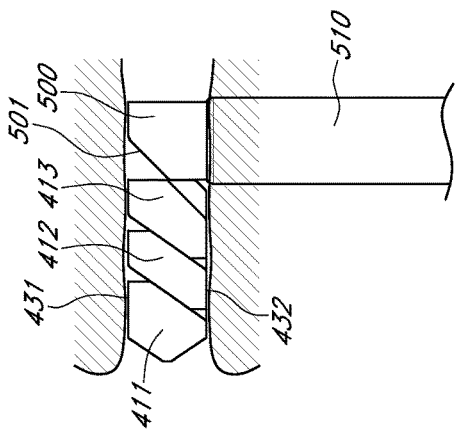
Figure 6C:
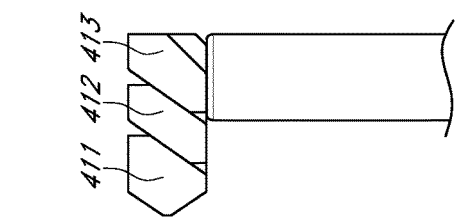
Figure 6D:
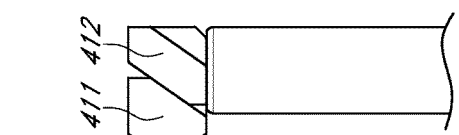
Figure 6E:
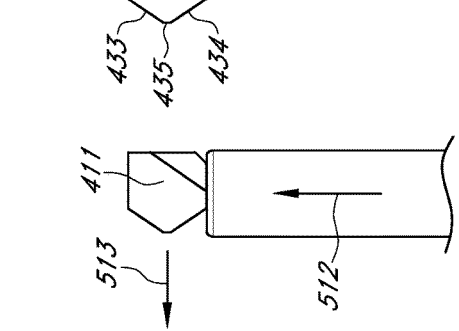

In some examples, once the plurality of wedge components 410 are installed in the disc space as illustrated in FIG. 6D, the ramped insertion tool 500 may be rotated as illustrated in FIG. 6E. In some examples, the insertion tool 500 is configured so that rotation of the insertion tool 500 forces the plurality of wedge components 410 even further radially outward in the second direction 513. In another example, rotation of the insertion tool 500 may sever a means for retaining the $3^{rd}$ wedge component 413 to the insertion tool 500. In another example, rotation of the insertion tool 500 continues to advance the spinal implant radially.

In some examples, the wedge system cannula 510 is circular in cross section. In some examples, the inner diameter of the wedge system cannula 510 is between approximately 9 mm and 15 mm. In some examples, the plurality of wedge components 410 are circular in cross section. In some examples, the ramped insertion tool is circular in cross section. In some examples, the outer diameter of the plurality of wedge components 410 and ramped insertion tool 500 is between approximately 9 mm and 15 mm. In some examples, the height, or the distance between the top surface 431 and the bottom surface 432, of the plurality of wedge components 410 is approximately 7 mm to 17 mm. In some examples, the height of the wedge components 410 may vary. In some examples, the wedge components 410 in the system are able to maintain lordotic angles of approximately 0 degrees to 10 degrees. In some examples, the wedge components 410 may include a void/windows configured to accept graft material. In some examples, the wedge components may include tantalum marks for visualizing the disc space during and after insertion. In some examples, the spinal implants comprise endplate-contacting surfaces configured with angled teeth or ridges for device retention.

In some examples, portions of the wedge system 400 may be made from a variety of biocompatible materials which may include, for example, metal, titanium, stainless steel, Nitinol, purolitic carbon, polymers, polyether ether ketone, and other biocompatible materials known in the art.

In yet another aspect and example, a trans-sacral spinal implant serves as an analog to cages used in TLIF procedures. With reference to FIGS. 3A-3D, 4A-4D, and 10, there is illustrated a trans-sacral spinal implant for insertion from anterior target site on the surface of the sacrum into a disc space, the implant having a length between a leading end and a trailing end, the length sufficient to contact each of two adjacent vertebrae; each of the leading end and trailing end including engagement surfaces 301, e.g., such as "teeth" or ridges, configured to engage endplates of the adjacent vertebrae and the implant having a width that is less than about 15 mm. In one aspect, one or multiple cages in any radial direction (anterior, anterio-lateral, lateral, posterior). In another aspect, a taller cage may be deployed in an anterior direction for lordosis and a shorter cage or cage construct may be deployed posterior. In still other aspects, the cage(s) may comprise: a lordotic angle(s) to fit L5/S1 endplate angle; a wedge design to self-distract disc space as it is being inserted; voids/windows for graft material; tantalum marks for visualizing in the disc space during and after deployment; materials configured from PEEK, allograft, titanium, tantalum, cobalt chrome, or combinations thereof In still another aspect and example, as illustrated in FIGS. 11A-11C, a trans-sacral spinal implant 300 for insertion from an anterior target site on the surface of the sacrum into a disc space comprises an arched shaped body 350 configured to navigate and facilitate an approximately 90 degree turn from axial access to lateral/radial deployment during insertion into the disc space, the arched shaped body 350 having a leading end 351 and a trailing end 352; the trailing end 352 including a pivotable connection 353 to an insertion device 354. In this example, the height of the spinal implant 300 is about equal to/determined by the inner diameter of the cannula 304 through which it is inserted for deployment. The attachment point 355 to insertion tool 354 allows rotation so the trans-sacral spinal implant 300 can make the turn. In some examples, an insertion tool 354 may also have a spring to assist the trans-sacral spinal implant 300 in making the 90° turn.

Figure 12:
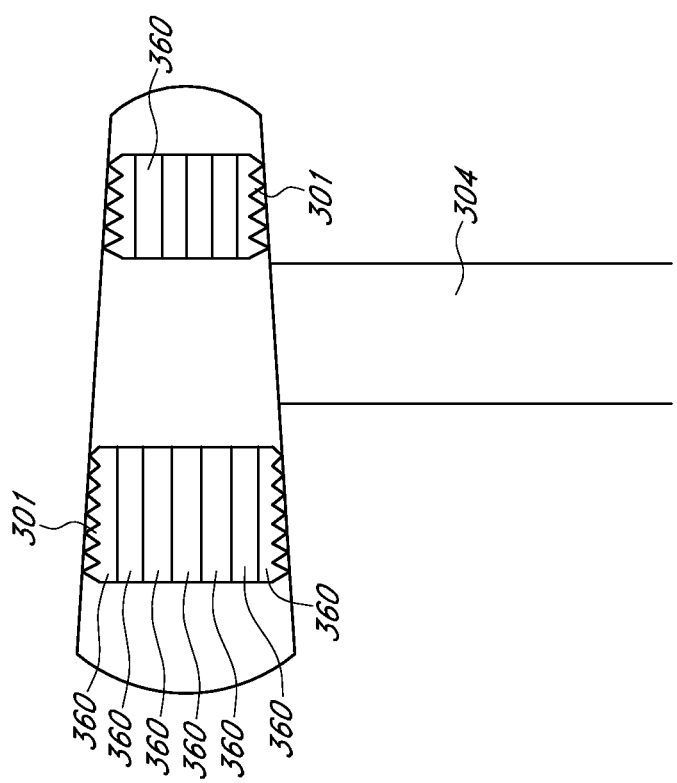
FIG. 12 shows stacks of multiple, wafer-like implants
Figures 13A, 13B:
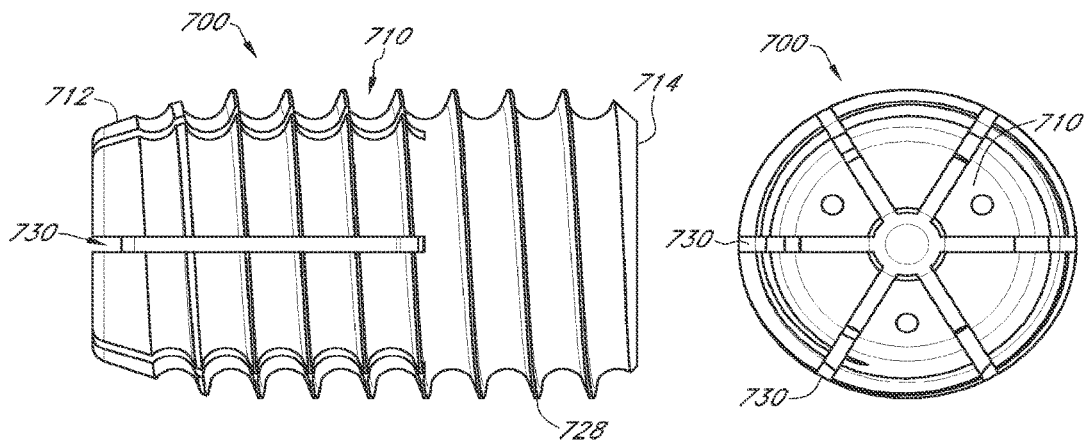
FIGS. 13A-13D illustrate a 2-piece expandable plug inserted into the sacral access bore (plug does not extend into disc space)
Figure 13C:
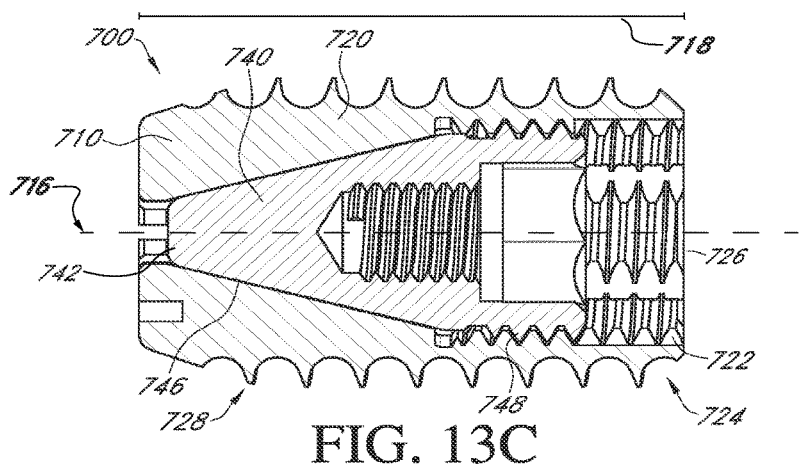
Figure 13D:
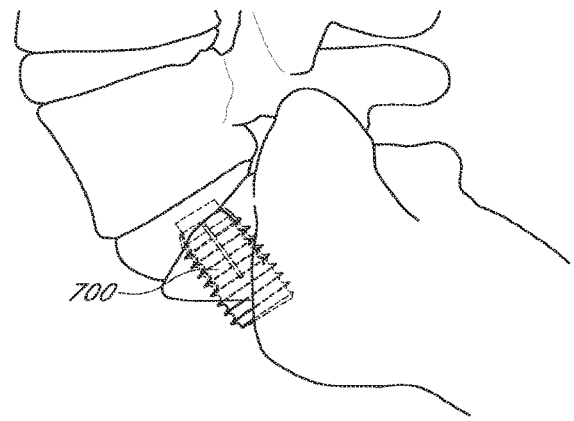
Figure 15A:
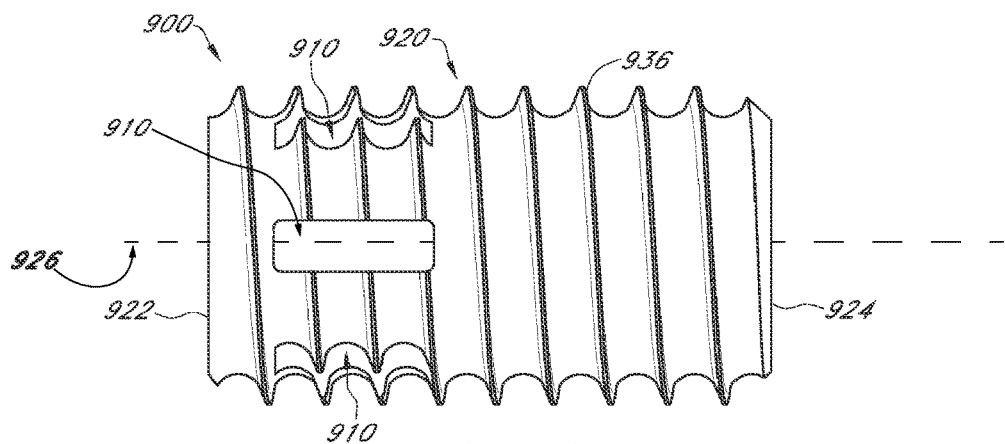
FIGS. 15A-15F illustrate a 1-piece threaded cage comprising windows which carry bone graft material, and configured to maximize the device's "L-5 footprint" for axial/compressive load support and distribution
Figure 15B:
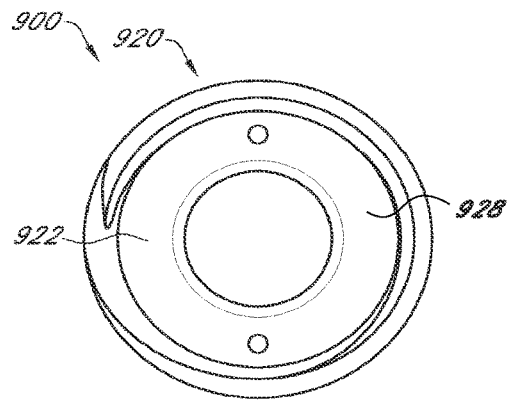
Figure 15C:
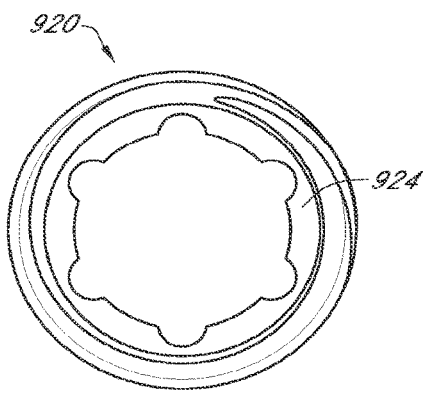
Figure 15D:
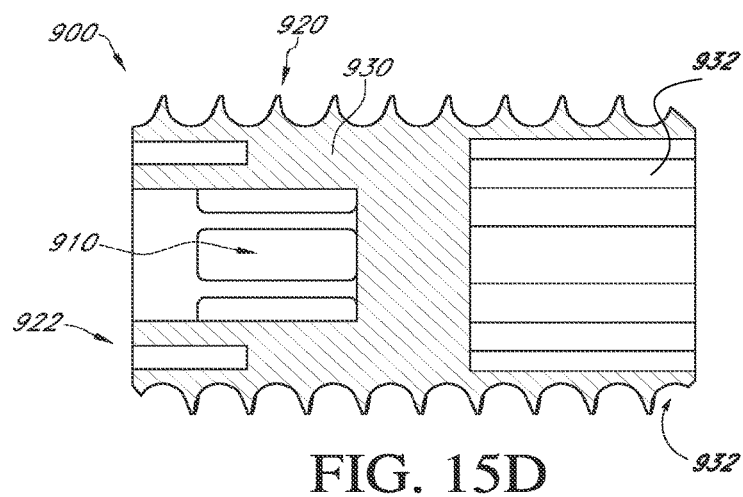
Figure 15F:
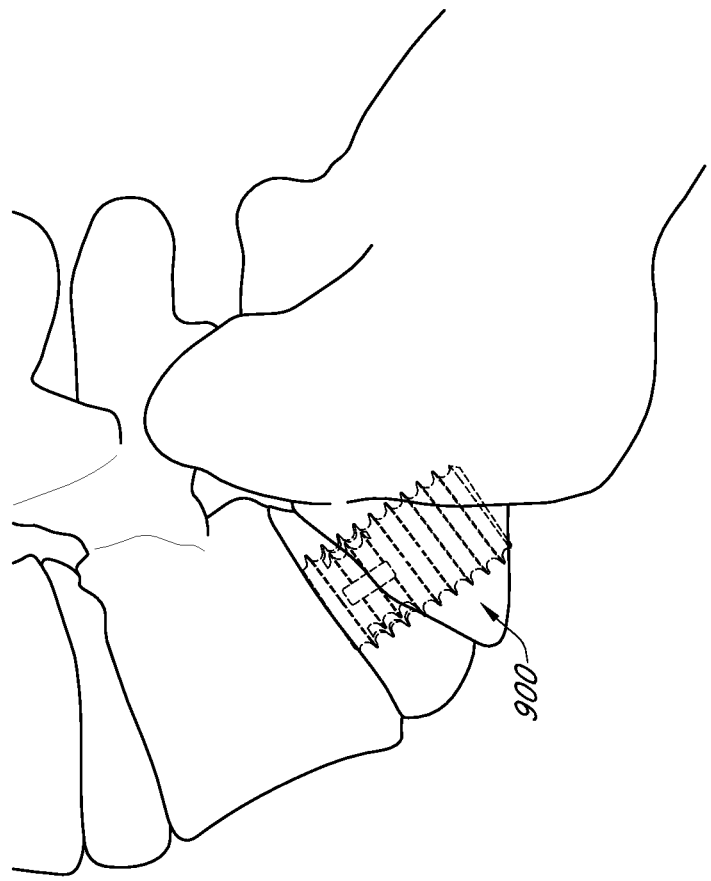
Figure 15E:
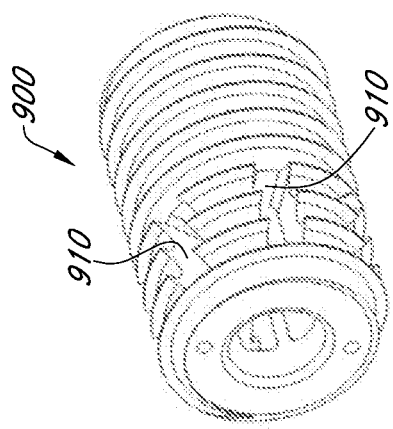
Figures 16A, 16B:
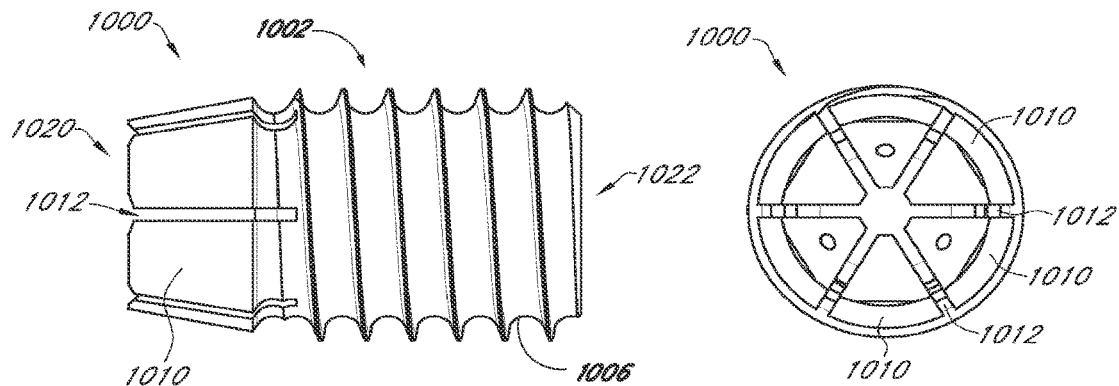
FIGS. 16A-16H show one example of a threaded spinal cage that is configured as an expandable "flower, e.g., with a plurality of "petals" at a distal end of the implant
Figure 16C:
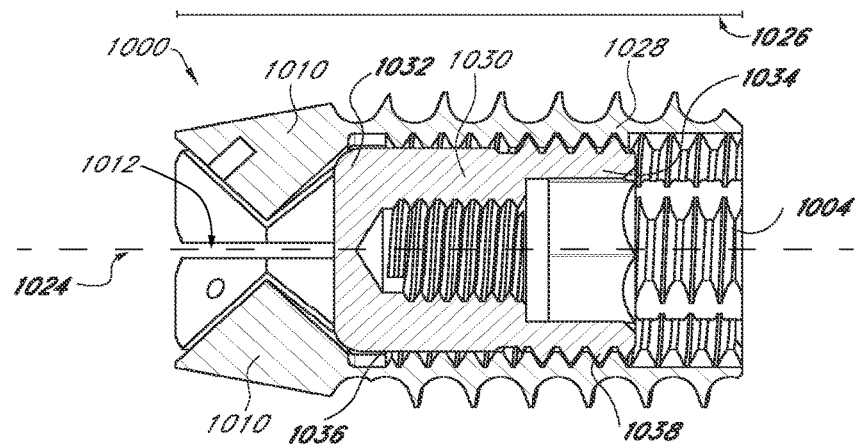
Figure 16D:
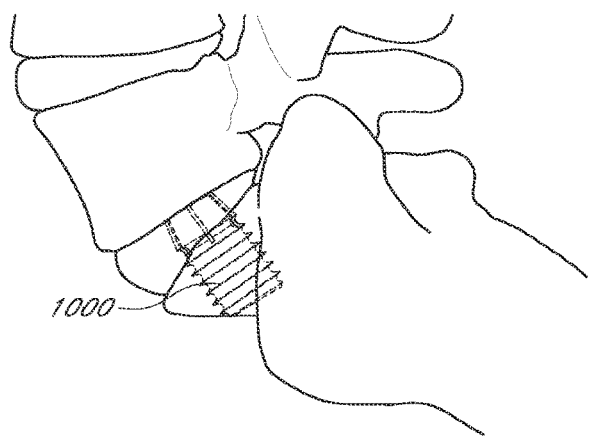
Figure 16E:
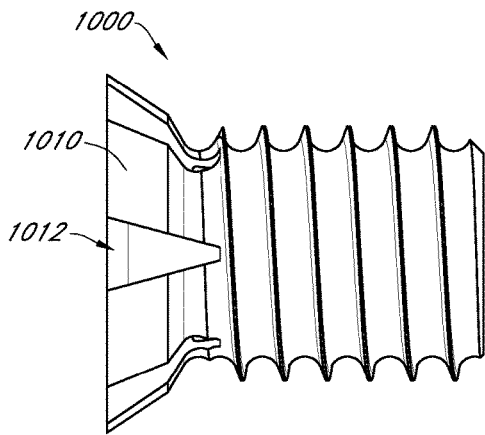
Figure 16F:
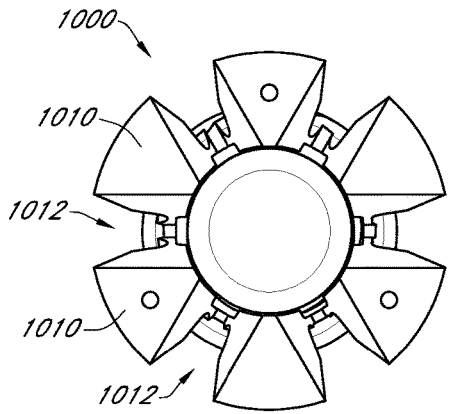
Figure 16G:
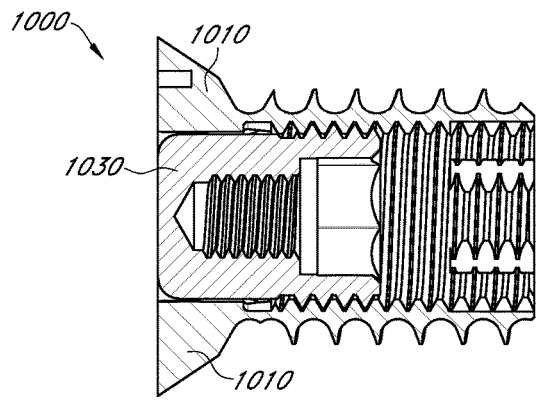
Figure 16H:
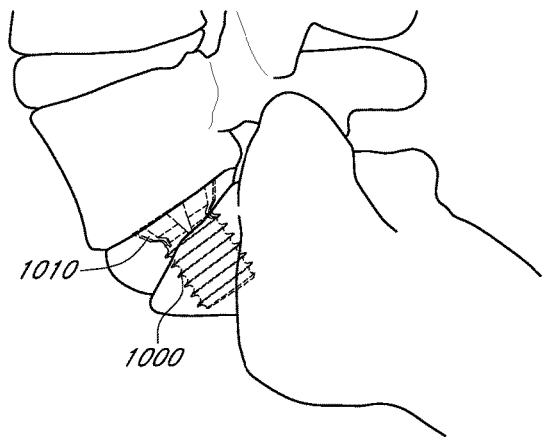

In yet another aspect and example, with reference to FIG. 12, a spinal implant construct/system 300 is configured and deployed to comprise a stack of individual wafer-like devices 360, parallel to a vertebral endplate(s). In some examples, stacking one or multiple constructs 360 to different heights permits accommodation or creation of lordosis. In another aspect and example, a benefit is an ability to achieve a gradual distraction. For example, if a height of a disc space is 7 mm and distraction to 11 mm is needed, a surgeon could gradually add wafers 360 in 1 mm height increments to eventually get to the 11 mm height, as opposed to having to deploy a single height 11 mm cage and achieve 4 mm of distraction in one push. Moreover, by gradually stacking wafers 360 the surgeon is able to press fit each construct to match the height of that particular portion of the disc, and can in the manner create or maintain lordosis, e.g. by deployment of more wafers 360 in the anterior portion of a disc as compared to posterior portion of the disc.

In still another aspect, with reference to FIGS. 3E-3F and FIGS. 4A-4D, in some examples a trans-sacral spinal implant 320 for insertion from an anterior target site on the surface of the sacrum into a disc space; the implant 320 comprises a pair of semi-circular intervertebral cages configured from, for example, PEEK, that together form a cylindrical shape, the pair of semi-circular intervertebral cages being joined together by a spring 325 configured, for example, from Nitinol. In some examples, two PEEK components that are connected by a flexible nitinol spring 325 bend together to allow the spinal implant to fit through the inner diameter of a deployment cannula/insertion tool. Once the spinal implant 320 emerges from the distal end of the cannula 304, the nitinol spring 325 comprised as part of the spinal implant straightens out as it is deployed into the disc space, and the PEEK components serve to bear compressive loads, e.g., between the end plates.

In still another aspect of the present disclosure, with reference to FIGS. 13A-13D, a 2-piece expandable plug 700 is inserted into the sacral access bore (does not extend into disc space). In one aspect of the spinal implant system 700 of the present disclosure, a PEEK plug is also implanted to lock the spinal cage deployed into a disc space and prevent it from migrating back out of an access channel. In another aspect and example, a plug such as depicted above may be used following a "soft fusion" procedure, e.g., where a discectomy is performed and the disc space is filled with bone graft/growth media, to prevent the graft material from "leaking" back out of the disc space. In another aspect and example, a plug is inserted following a revision surgery, for example, to remove a previously implanted AXIALIF® implant 100. In some examples, a trans-sacral spinal implant 700 for insertion from an anterior target site on the surface of the sacrum into the sacrum comprises a first body 710 having a leading end 712, a trailing end 714, a longitudinal axis 716 through the leading and trailing ends, a length 718 parallel to the longitudinal axis, and a sidewall 720 surrounding the longitudinal axis and extending from the leading end to the trailing end, the first body 710 having an interior surface 726 and an opposite exterior surface 724; a first thread 722 extending along the interior surface 726 of the first body 710 and an exterior thread 728 on the exterior surface of the first body; leading end 712 of the first body 710 including at least one slot 730 extending from the leading end 712 of the first body 710 towards the trailing end 714; the at least one slot 730 extending from the exterior surface 724 to the interior surface 726; a second body 740 having a leading end 742, a trailing end 744 and an exterior surface 746 extending from the leading end 742 to the trailing end 744, the exterior surface 746 comprising an exterior thread 748 that engages the interior thread 722 of the first body 710; wherein threading the second body 740 into the interior surface 726 of the first body 710 causes the leading end 712 of the first body 710 to radially expand.

In yet another example, with reference to FIG. 14C, a 1-piece, non-expanding plug 800 comprises radio-opaque markers 810 on or in a wall of a leading edge to facilitate device placement (e.g., using fluoroscopy) is used for the purposes as just described above for the 2-piece expanding plug 700 (see also caption for FIGS. 13A-D) and in one example, is fabricated from PEEK. In some examples, the device 800 may comprise internal retention threads 820; a graft chamber 830; a "blind" hole 840 in the leading end.

In one aspect of the present disclosure, a trans-sacral spinal implant for insertion from an anterior target site on the surface of the sacrum into the sacrum comprises a first body having a leading end, a trailing end, a longitudinal axis through the leading and trailing ends, a length parallel to the longitudinal axis, and a sidewall surrounding the longitudinal axis and extending from the leading end to the trailing end, the first body having an interior surface and an opposite exterior surface; a first thread extending along the interior surface of the body and an exterior thread on the exterior surface of the first body; a second body having a leading end, a second and an exterior surface extending from the leading end to the trailing end, the exterior surface comprising an exterior thread that engages the interior thread of the first body.

In still another aspect and example, with reference to FIGS. 15A-F, a 1-piece threaded cage 900 comprises (e.g., radial) windows 910 or apertures 910 which carry bone graft material, and is configured to maximize the device's "L-5 footprint" for axial/compressive load support and distribution. In some examples, the threaded cage 900 creates distraction according to the distance the cage 900 is advanced distally, and with axial force from the sacral bone to the outer thread of the mechanical interface and the "L-5 footprint." In some examples, a trans-sacral spinal implant 900 for insertion from an anterior target site on the surface of the sacrum into the sacrum comprises a first body 920 having a leading end 922, a trailing end 924, a longitudinal axis 926 through the leading and trailing ends, a length 928 parallel to the longitudinal axis 926, and a sidewall 930 surrounding the longitudinal axis 926 and extending from the leading end 922 to the trailing end 924, the first body 920 having an interior surface 932 and an opposite exterior surface 934 and an exterior thread 936 on the exterior surface 934 of the first body 920; the first body 920 including at least one aperture 910 extending from the exterior surface to the interior surface; the leading end 922 of the first body 920 forming a substantially flat distal surface that is substantially perpendicular to the exterior surface of the first body. In some examples, a spinal implant 900 comprises an aperture on a radial surface and on a top/distal face 928.

In another aspect and example, with reference to FIGS. 16A-H, a threaded spinal cage 1000 is configured as an expandable "flower," e.g., with a plurality of "petals" 1010 at a leading end 1020 of the implant that spread as an internal metal plug 1030 comprised as part of the cage 1000 interfaces with and engages internal threads in the threaded cage, the cage 1000 is advanced distally, up to but not into an inferior endplate of the L5 vertebral body. Each petal 1010 bends at an approximate angle of 45° to maximize contact with L5 endplate. In a preferred example, the threaded cage 1000 comprises between two and six petals 1010. In some examples, a threaded spinal cage 1000 with an expandable distal end is dimensioned with a major thread diameter range of between about 13 mm and about 15.5 mm and a length of between about 20 mm and about 40 mm. In some examples, a trans-sacral spinal implant 1000 for insertion from an anterior target site on the surface of the sacrum into the sacrum comprises a first body 1002 having a leading end 1020, a trailing end 1022, a longitudinal axis 1024 through the leading and trailing ends, a length 1026 parallel to the longitudinal axis, and a sidewall 1028 surrounding the longitudinal axis and extending from the leading end to the trailing end, the first body 1002 having an interior surface 1004 and an opposite exterior surface 1006; a first thread extending along the interior surface of the body and an exterior thread on the exterior surface of the first body; leading end of the first body including at least one slot 1012 extending from the leading end of the first body towards the trailing end; the at least one slot extending from the exterior surface to the interior surface, the leading end forming substantially flat distal surface that is substantially perpendicular to the exterior surface of the first body; a second body 1030 having a leading end 1032, a trailing end 1034, and an exterior surface 1036 extending from the leading end 1032 to the trailing end 1034, the exterior surface 1036 comprising an exterior thread 1038 that engages the interior thread of the first body 1002; wherein threading the second body 1030 into the interior surface of the first body 1002 causes the leading end of the first body 1002 to radially expand. In some examples, the bend is approximately 45 degrees to deploy the petals 1010 beyond the radial footprint of the thread major (diameter).

In yet another aspect and example, with reference to FIGS. 17A-H, a threaded cage 1100 is dimensioned and configured as a flower with petals 1110 as an example as described above, but the cage 1000 is also additionally configured for insertion into the L-5 endplate and vertebral body and comprises a different internal metal plug 1130 such that the distal tip 1132 of the metal plug 1130 comprises self-tapping bone threads 1134. In some examples, the length of the metal bone threads for L-5 is between about 10 mm and about 25 mm. As a metal plug 1130 advances via internal threads in a flower cage it opens the flower "petals" 1110 and also begins engaging with the L5 vertebral body. Once the internal plug 1130 is fixated to L5 and the "petals" are open, it affords the benefits of rigid fixation between L5 and S1 (advantageous for spondylolisthesis biomechanics and bending resistance) as well as better resistance to subsidence because the open "petals" resist any cage migration up into L5. In some examples, a trans-sacral spinal implant 1100 for insertion from an anterior target site on the surface of the sacrum into the sacrum comprises a first body having a leading end, a trailing end, a longitudinal axis through the leading and trailing ends, a length parallel to the longitudinal axis, and a sidewall surrounding the longitudinal axis and extending from the leading end to the trailing end, the first body having an interior surface and an opposite exterior surface; a first thread extending along the interior surface of the body and an exterior thread on the exterior surface of the first body; leading end of the first body including at least one slot extending from the leading end of the first body towards the trailing end; the at least one slot extending from the exterior surface to the interior surface, the leading end forming substantially flat distal surface that is substantially perpendicular to the exterior surface of the first body; a second body having a threaded leading end, a second and an exterior surface extending from the leading end to the trailing end, the exterior surface comprising a thread that engages the interior thread of the first body; wherein threading the second body into the interior surface of the first body causes the leading end of the first body to radially expand and for the threaded leading end to extend past the leading end of the first body.

Figure 18:
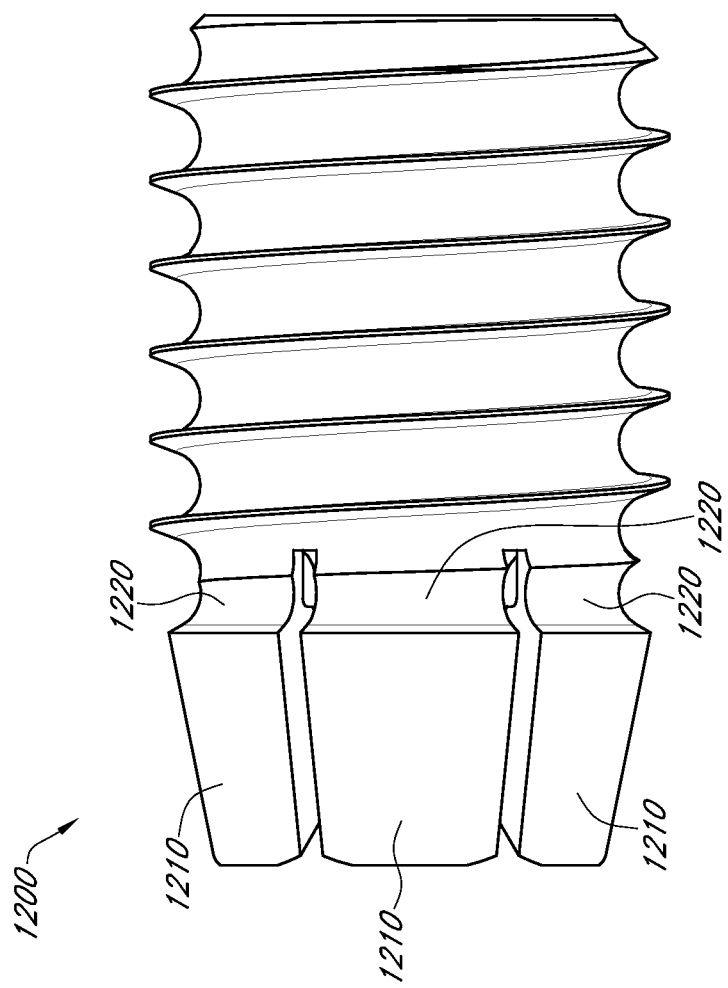
FIG. 18 depicts an example of a threaded cage configured as a flower with petals additionally configured to comprise Nitinol expandable joints

In yet another aspect and example, with reference to FIG. 18, a threaded cage 1200 configured as a flower with petals 1210 as described above additionally is configured to comprise Nitinol for the expandable joints 1220 to improve an ability of the threaded cage to withstand repeated loading cycles. In some examples, a segment of the device is configured with nitinol inserted between a PEEK threaded base and a PEEK "petal(s)", such that advancement of an internal metal plug deflects the petals 1210 outward in such a manner that the expandable joint 1220 bears the deflection and the load.

Figure 19B:
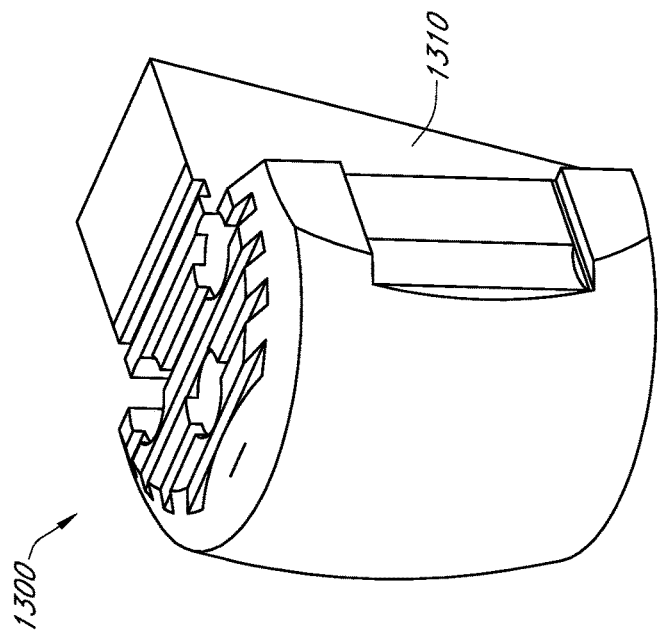
FIGS. 19A-19B show an example of a spinal cage configured with an angled or wedge-shaped posterior portion
Figure 19A:
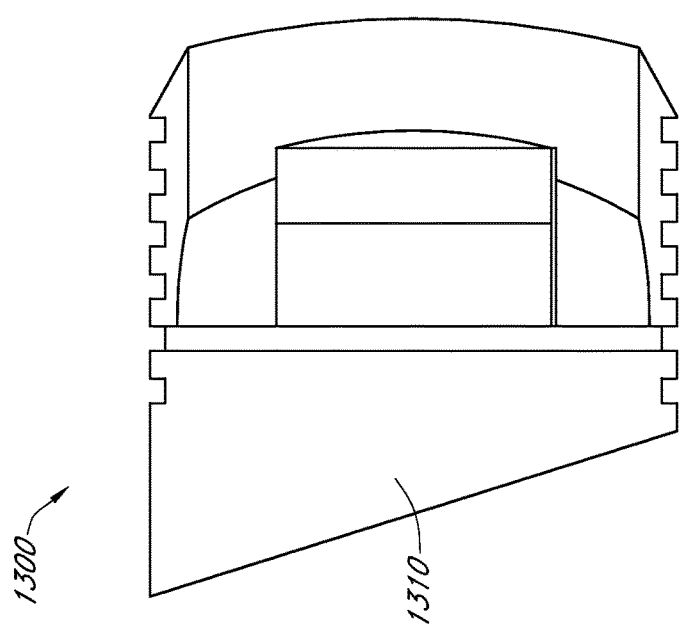

In another aspect an example, with reference to FIGS. 19A-19B, a mini-cage 1300 is configured to comprise an angled or wedge-shaped posterior portion 1310, which enables the cage 1300 to be deployed into a disc space using an axial tool 1320 to push the wedge shape in the radial direction. This example has an added advantage in that the cage 1300 may be expanded, e.g., in situ, in a modular manner to configure a larger device in a disc space of greater volume.

Figure 20:
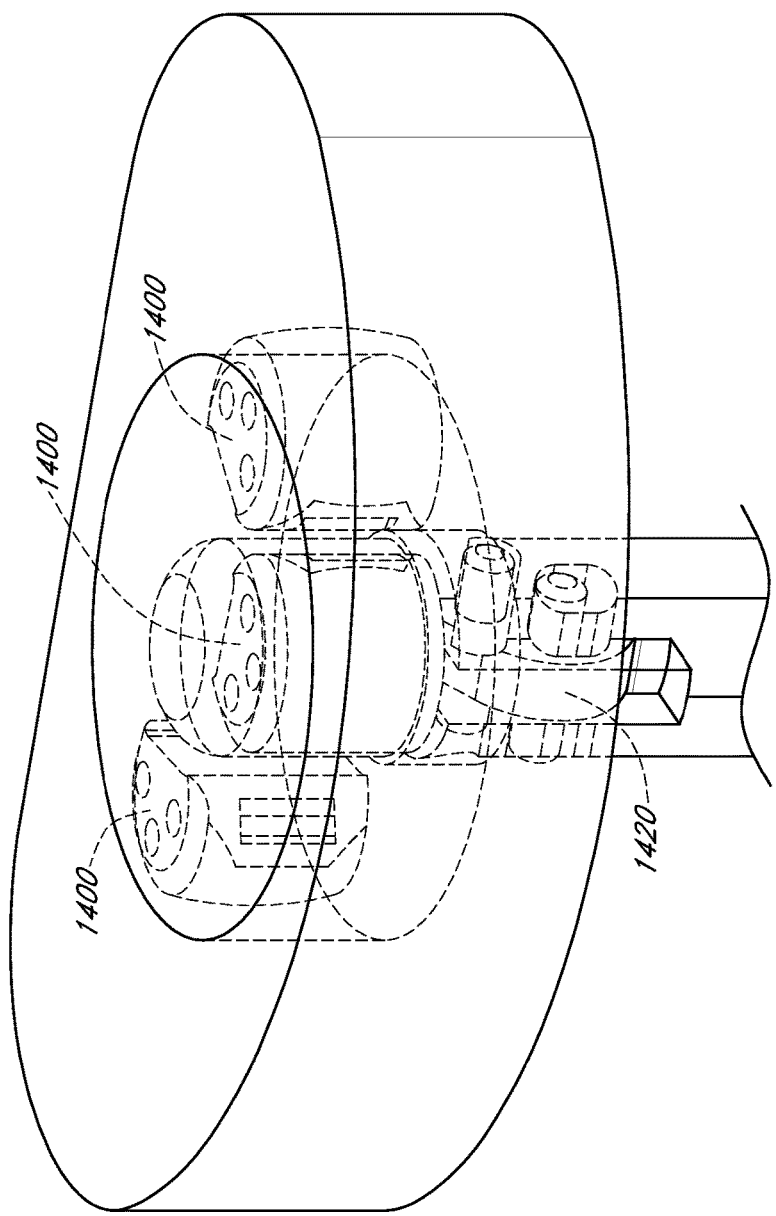
FIG. 20 shows an example of a cage with a non-wedged back, deployed by means of rotating a cam tool

In still another aspect and example, with reference to FIG. 20, a mini-cage 1400 is configured with a non-wedged posterior portion 1410, and the cage 1400 is inserted by means of a cam tool 1420 that is then rotated to deploy the cage 1400 radially into a disc space.

Figure 21B:
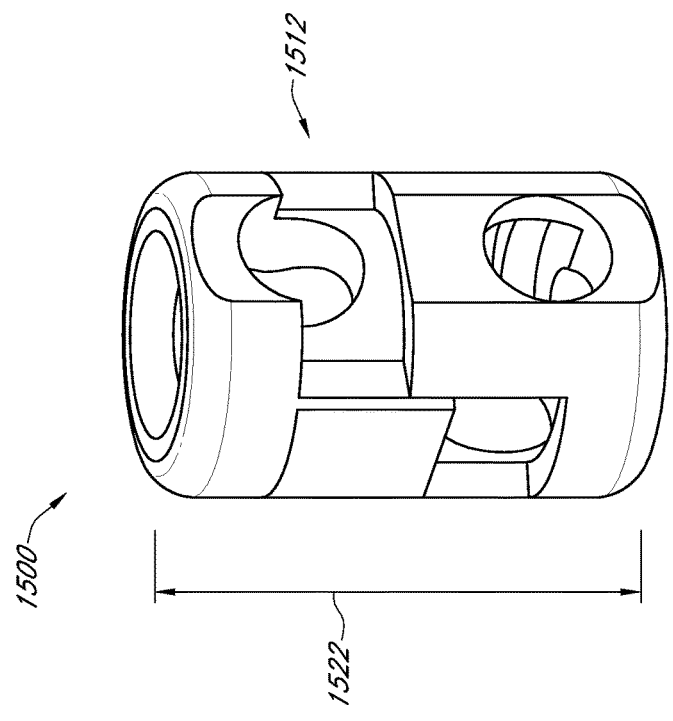
FIGS. 21A-21B shows a mini-cage example which is configured as an expandable device that in an expanded configuration distracts a disc space
Figure 21A:
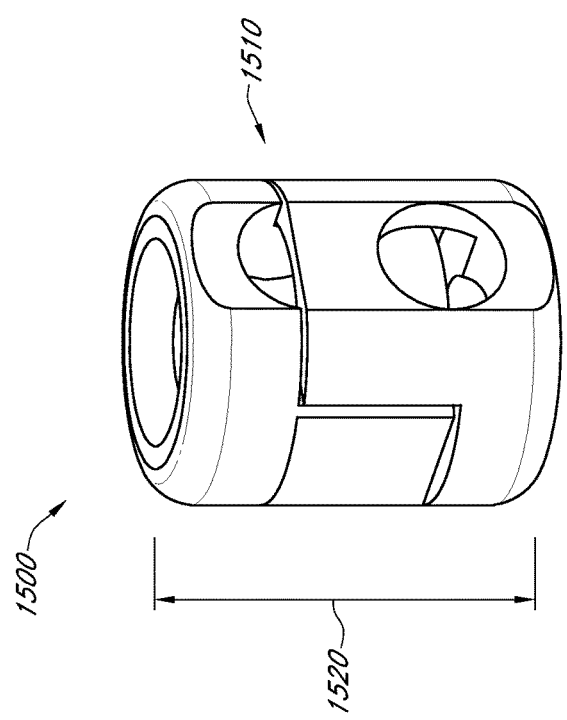

In yet another example, with reference to FIGS. 21A-21B, a mini-cage 1500 is configured as an expandable device that in an expanded configuration 1512 distracts a disc space. An advantage of this configuration is that it allows for deployment of multiple devices of one initial height 1520 which are then variably adjustable within the disc space as needed, thereby accommodating lordosis. In one aspect, devices 1500 are provided in the non-expanded configuration 1510 in sizes (heights) 1520 of between about 5 mm and about 9 mm in increments of 1 mm, each with an ability to expand to about 1.5 times the height of the collapsed or non-expanded configuration 1510. In another aspect, the diameter 1524 of the cage is configured to conform/be deployable through the inner diameter of the current axial access cannula 1530 being used, between about 9 mm and about 15 mm In another example, with reference to FIGS. 22A-22C and 23A-23B, a mini-cage 1600 is configured as a hollow sphere with a plurality of exterior sides 1610 or surfaces, and may be fabricated from, for example PEEK, Allograft or a medical grade implantable metal or metal alloy. In another aspect, the interior 1620 of the hollow sphere can be filled with bone graft 1630 or an osteoconductive material 1632 to promote bone growth between vertebral bodies in the motion segment and also allow bone to grow into the porous surface of the cage. An advantage of this example is that a plurality of cages 1600 of diameters between about 3 mm and about 17 mm may be deployed without regard to cage orientation or inserter position. Another advantage is that multiple cages 1600 of varying sizes may be deployed to create a wedge effect, which has utility as a lordosis therapy, for example, with the largest cage positioned in the anterior portion of the disc space and with progressively descending cage sizes deployed towards the posterior portion of the disc space. In another aspect and example, due to their geometries, the insertion of a plurality of spherical cages of varying diameters allows them to interlock and provide structural support to the disc.

Figure 24:
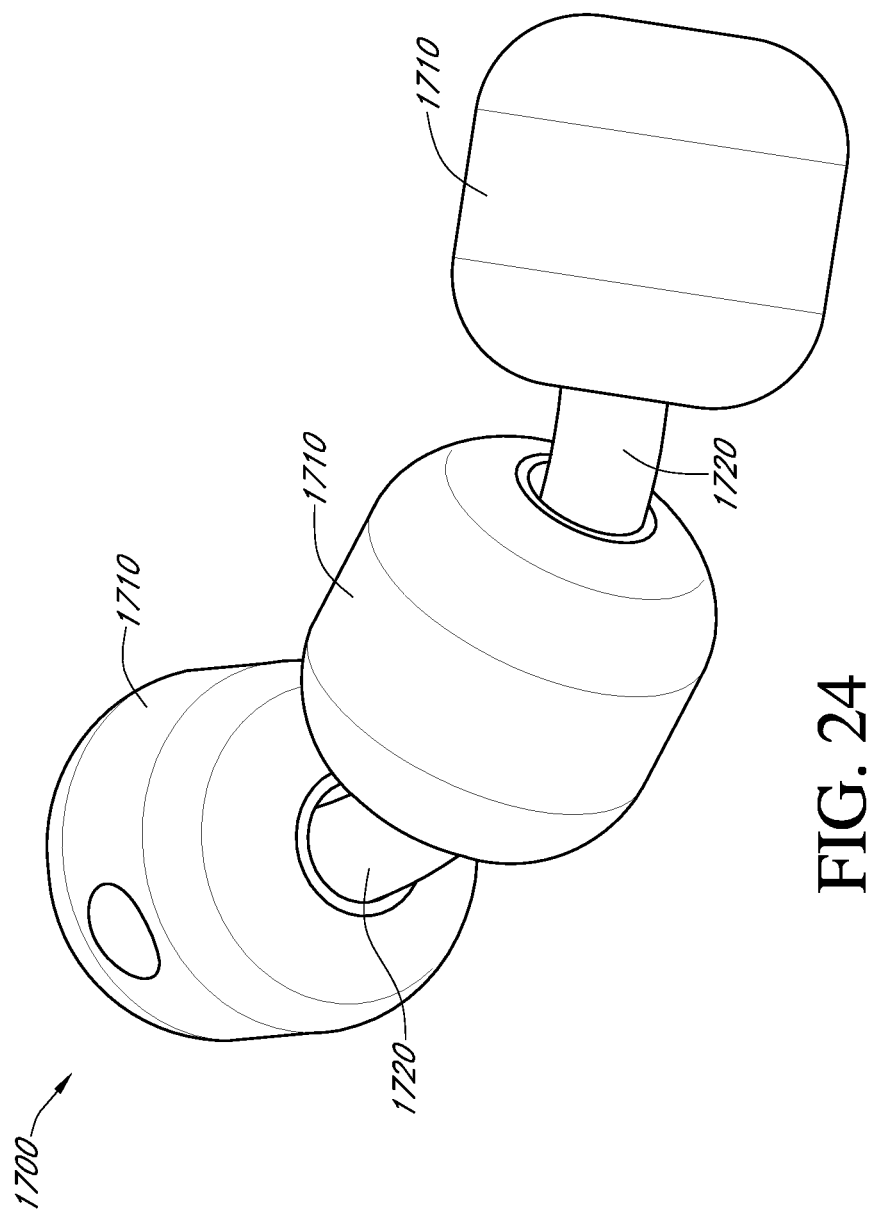
FIG. 24 illustrates an example of a modular, "connected" cage
Figure 25G:
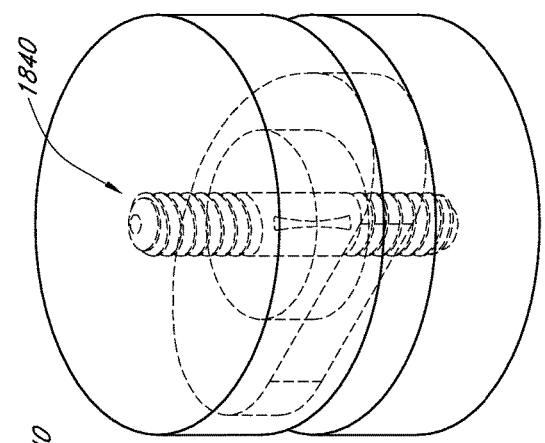
Figure 25F:
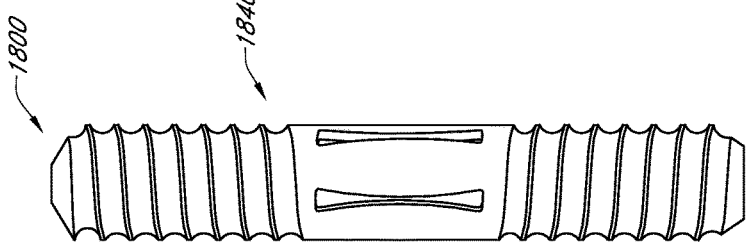
Figure 25E:
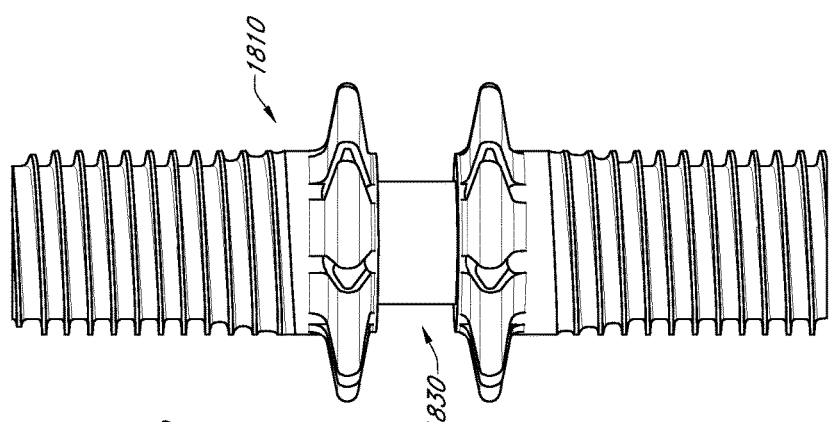
Figure 25D:
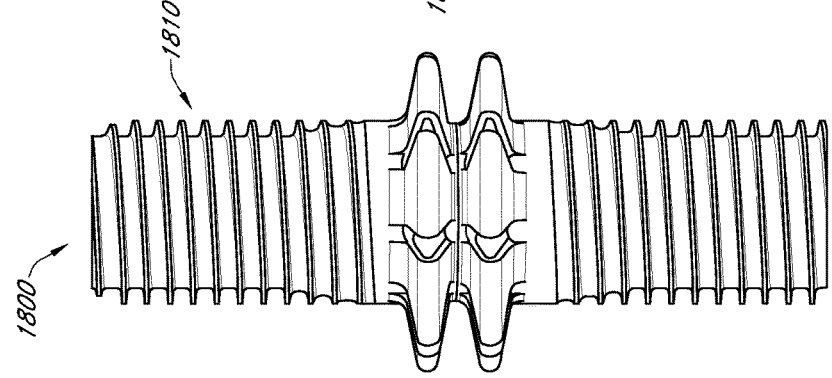

In still another example, with reference to FIG. 24, a mini-cage system 1700 comprises a plurality of connected devices 1710, the shape of which is configured to facilitate deployment into the disc space as a single unit, progressively inserted/pushed out into the disc space. In some examples, an individual modular cage 1710 is connected to a neighboring cage 1710 by means of a flexible wire 1720 fabricated, for example, from nitinol or stainless steel. In another aspect and example, the flexible wire 1720 is able to be adjusted, aspect, the diameter of the device 1700 ranges from between about 5 mm up to the diameter of the access bore drilled into the vertebral body into the disc space. In another aspect and example, a device diameter 1730 is determined by the (available) disc space height, and is further configured for ease of deployment from axial insertion to radial deployment In another example, with reference to FIGS. 25A-25G, a spinal implant 1800 is configured to be an expandable, winged cage 1810 upon deployment, and comprises a first anchor portion 1820 and a second anchor portion 1822 at opposing distal 1812 and proximal 1814 ends of the cage, and an intermediate inner member 1830 that serves as a distraction device. In one aspect, the device 1800 is inserted in a first non-expanded/un-winged configuration 1808, which upon compression of at least one of the anchors 1820, 1822, the outer diameter of the anchor deforms, radially creating "wings" or flanges. In some examples, the implant 1800 may then be further expanded by rotating an inner member 1832, e.g., by means of threads, to either engage a vertebral endplate, or upon further rotation and advancement, to distract the motion segment. In yet another example, also shown in FIG. 25F, the winged cage 1840 is configured as a non-expanding, non-distraction device.

Of course, the foregoing description is of certain features, aspects and advantages of the present invention, to which various changes and modifications can be made without departing from the spirit and scope of the present invention. Thus, for example, those of skill in the art will recognize that the invention can be embodied or carried out in a manner that achieves or optimizes one advantage or a group of advantages as taught herein without necessarily achieving other objects or advantages as can be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different examples can be made and still fall within the scope of the invention. Accordingly, it should be understood that various features and aspects of the disclosed examples can be combined with or substituted for one another in order to form varying modes of the discussed devices, systems and methods (e.g., by excluding features or steps from certain examples, or adding features or steps from one example of a system or method to another example of a system or method).

Component Details.

Materials Choices

Choices for material for use in the various components comprised in the constructs shown herein are machinable and medical grade, and include but are not limited to, e.g., machinable allograft, PEEK, titanium or titanium alloys, cobalt-chromium alloys, and stainless steel alloys, Nitinol, or combinations thereof. These biocompatible materials can withstand sterilization techniques such as Ethylene oxide (EtO) gas, radiation, steam autoclaving, dry heat, and cold sterilization. Other desirable attributes are that the material is able to be imaged, e.g., visible via fluoroscopy, X-ray and/or computed tomography (CT); dimensionally stable, and with sufficient biomechanical properties (strength, stiffness, toughness) for intended use, e.g., is sufficiently stiff to allow a relatively thin wall. If needed, materials may be used with incorporated visualization markers, e.g. tantalum, although other materials may be used. The selected material(s) may be able to undergo surface treatments, such as bead blasting to promote anti-slippage, or surface coating, e.g., with hydroxyapatite (HA), or roughening to promote bone in-growth.

Provision of Therapy

After creating access to the targeted spinal vertebra and/or discs, and aligning or stabilizing/fixing them using the methods as disclosed herein, additional therapy may be provided. One form of therapy is to fuse the selected spinal levels together. Spinal fusion typically involves the use of osteogenic, osteoconductive, or osteoinductive material (bone graft). One process to promote fusion is to insert quantities of one or more fusion promoting materials into the areas to be fused, or into openings in certain examples of the spinal cages described in the present disclosure. Bone graft is the material that is used to promote bone growth and forms the scaffold that bridges the adjacent vertebral bodies comprising a motion segment in the spine. The fused portions of the vertebrae do not move with respect to one another. It is useful to have one name for the variety of materials used to promote fusion. Thus, fusion promoting materials including osteogenic, osteoconductive, and/or osteoinductive material are collectively described herein as bone graft, whether the material is autograft or allograft and various bone graft substitutes or bone graft extenders. Various techniques for promoting effective fusion of adjacent vertebrae are well known to those of skill in the art so a minimal summary is sufficient for this document. The spinal cage devices of the present disclosure may be used in conjunction with bone graft types that are autologous or allogenic, e.g., grafts from the iliac crest, rib, or tibia/fibula donor sites. Autograft, a combination of autograft and allograft, or allograft alone may be used.

Method of Use Examples

While the particulars of the tools for deployment of the implants are briefly illustrated herein, a detailed description is beyond the focus of this Provisional application although the implant deployment tools (e.g., insertion tools; retention tools; extraction tools, and tools that may be used for both insertion and extraction) are contemplated As used herein in this disclosure and application, it will be understood that the terms insertion tool, retention tool and extraction tool are sometimes used interchangeably or collectively and refer to the movement and manipulation of a spinal implant of the present disclosure. Moreover, it will be understood that a tool may serve individual and/or multiple purposes. A brief outline of the intended method of use/deployment of certain devices of the present disclosure is provided below.

Example A: Mini-Cage with AXIALIF®

Access and establish trajectory using dissector and beveled guide pin
6 mm, 8 mm, 10 mm dilator and sheath
9 mm drill through sacrum
L5/S1 discectomy using AXIALIF® discectomy tools (insert initial graft material)
12 mm dilator and sheath
10.5 mm drill through sacrum
Advance sheath opening to S1 endplate
Deploy mini-cage(s) (All concepts)
May deploy one or multiple cages (or cage constructs) in any radial direction (anterior, anterio-lateral, lateral, posterior)
May deploy taller cage or cage construct in anterior direction for lordosis and shorter cage or cage construct posterior
Cage may have lordotic angle to fit L5/S1 endplate angle
Cage may have wedge design to self-distract disc space
Dimensional Ranges:
Diameter for deployment through a tube=9 mm –15 mm (this would cover deployment 10 mm sheath up to tubular retractor); Height=7 mm–17 mm; Lordotic Angles –0°-10°
Insert secondary graft material around cages if this was not done in step 4
Continue with AXIALIF® procedure—Advance 12 mm sheath to L5 endplate Drill or dilate L5 endplate
Measure
Remove 12 mm sheath
Exchange bushing and tubular retractor with fixation wires
Insert AXIALIF
Remove tools and close incision Example B: Mini-Cage with Expanding Sacral Plug or Axial Threaded Cage Same steps as 1-9 in method described for Example A, above
Measure sacral length for plug length
Remove 12 mm sheath
Exchange bushing and tubular retractor with fixation wires
Insert Expanding Sacral Plug or Threaded Cage
If Expanding Sacral Plug (PEEK):
1. Insert until flush with superior S1 endplate (fluoroscopy marker on tip of plug will indicate)
2. Insert expansion arbor (metal), to expand plug and make it press fit inside of sacral bore. Expansion arbor engages internal threads of plug to push open the expanding "fingers" of the plug.
If Axial Threaded Cage (Simple 1-Piece PEEK)
1. Pack threaded cage with graft material
2. Insert threaded cage until flush with inferior L5 endplate
If Axial Threaded Cage (Flower Design with no fixation)
1. Insert Flower cage with internal expansion plug inside until the cage is flush with the inferior L5 endplate.
2. Rotate the internal expansion plug until the "petals" of the flower expand radially. Expansion plug engages internal threads of flower cage to push open the expanding "petals" of the cage.
3. May need to drive the entire expanded flower up to make secure contact with inferior L5 endplate.
If Axial Threaded Cage (Flower Design with fixation)
1. Insert Flower cage with internal expanding fixation plug inside until the cage is flush with the inferior L5 endplate.
2. Rotate the internal expanding fixation plug until the "petals" of the flower expand radially and the bone threads of the expanding fixation plug self-tap into the L5 vertebral body. Expansion plug engages internal threads of flower cage to push open the expanding "petals" of the cage.
Remove tools and close incision Example C: "Soft" Fusion* with Expanding Sacral Plug or Threaded Cage Access and establish trajectory using dissector and beveled guide pin
6 mm, 8 mm, 10 mm dilator and sheath
9 mm drill through sacrum
L5/S1 discectomy using AXIALIF® discectomy tools (insert primary graft material)
12 mm dilator and sheath
10.5 mm drill through sacrum
Advance 12 mm sheath to inferior L5 endplate using 12 mm tamp (packs bone radially)
Measure sacral length for plug length
Remove 12 mm sheath
Exchange bushing and tubular retractor with fixation wires
Insert Expanding Sacral Plug or Threaded Cage (See steps 5.1 through 5.4 in method in Example B, above)
Remove tools and close incision
Soft fusion is generally discectomy followed by insertion of bone graft/growth media without accompanying implant within disc space, and often in conjunction with posterior fixation and/or posterior fusion Example D: Revision with Expanding Sacral Plug Access and establish a guide wire in the back the AXIALIF® implant
Exchange bushing and tubular retractor with fixation wires
Remove AXIALIF® implant
Additional L5/S1 discectomy using AXIALIF® discectomy tools if desired
Pack L5 void and disc space with more graft material
Insert Expanding Sacral Plug
Insert until flush with superior S1 endplate (fluoroscopy marker on tip of plug will indicate)
Insert expansion arbor (metal), to expand plug and make it press fit inside of sacral bore. Expansion arbor engages internal threads of plug to push open the expanding "fingers" of the plug.
Remove tools and close incision
Alternatives and Variations
One of skill in the art will recognize that alternative variations may be contemplated for the examples presently disclosed that may achieve equivalence in intended function
Multi-Level Surgery
For convenience, the description set forth above provides therapy to stabilize vertebra or motion segment(s) via trans sacral access to the S1 sacral and L-5 lumbar levels however one of skill in the art will recognize that the process set forth above may applied to constructs so that more than one motion segment, in multiple spinal levels (e.g., L5-L4) may receive therapy (such as subsequent deployment of bone growth media and fusion) during a single surgical intervention.
Kits
One of skill in the art will recognize that the surgical procedures set forth above may benefit from various kits of tools and components for use in these procedures. Kits may focus on reusable or disposable components for creating an access route. Other kits may focus on the tools for preparing the targeted surgical site(s). A kit may include many (possibly even all) the components necessary for a particular procedure including the components needed to create the access route, prepare the targeted sites and even an assortment of implants, as well as the instruments needed for their deployment.
One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art. Individual claims may be tailored to claim particular examples out of the array of examples disclosed above. Some claims may be tailored to claim alternative examples rather than preferred examples. Some claims may cover an embodiment set forth above with a modification from another example as the present disclosure does not include drawings of all possible combinations of feature sets.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

FIG. 1 shows the various segments of a human spinal column as viewed from the side.

Figure 2A:
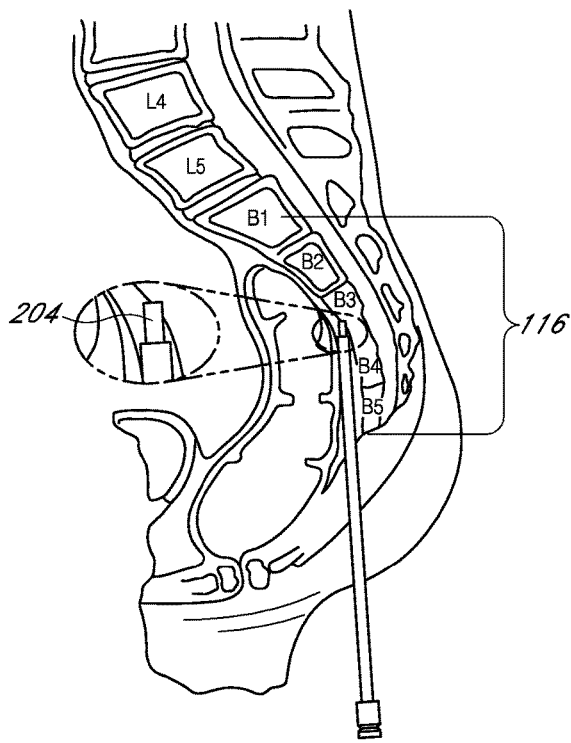
FIGS. 2A and 2B show axial trans-sacral access to the lumbo-sacral spine
Figure 2B:
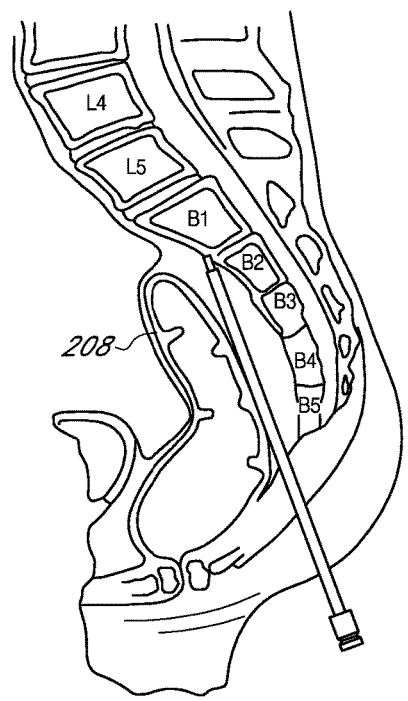
Figure 2C:
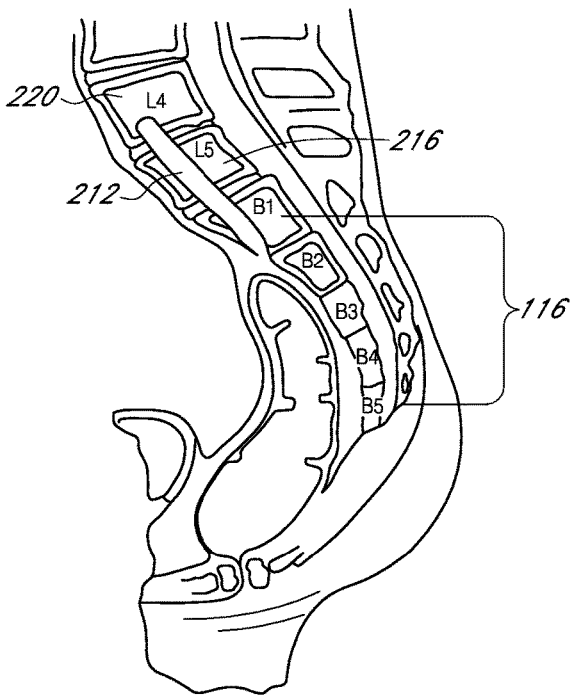
FIG. 2C illustrates a representative axial trans-sacral channel

FIGS. 2A and 2B show axial trans-sacral access to the lumbo-sacral spine, an example of a process of "walking" a blunt tip stylet 204 up the anterior face of the sacrum 116 to the desired position on the sacrum 116 while monitored on a fluoroscope (not shown). FIG. 2C illustrates a representative axial trans-sacral channel 212 established through the sacrum 116, the L5/sacrum intervertebral space, the L5 vertebra 216, the L4/L5 intervertebral space, and into the L4 vertebra 220.

Figure 3D:
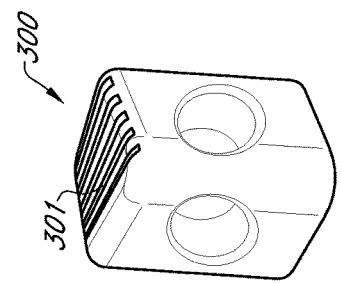
FIGS. 3A-3D show examples of representative "mini-cages"/spacers, including a "spring" cage
Figure 3C:
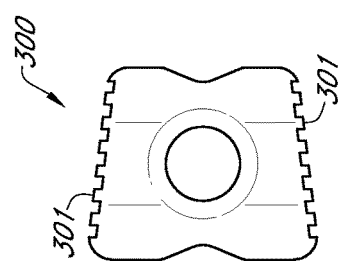
Figure 3B:
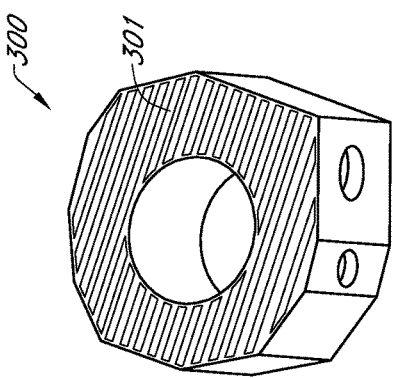
Figure 3A:
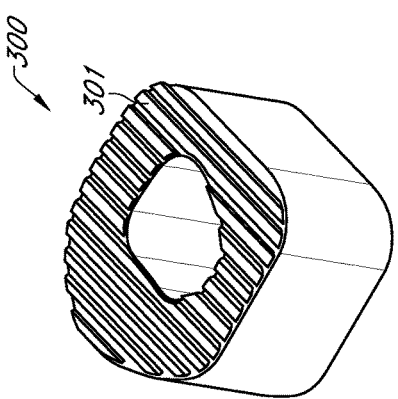
Figure 3E:
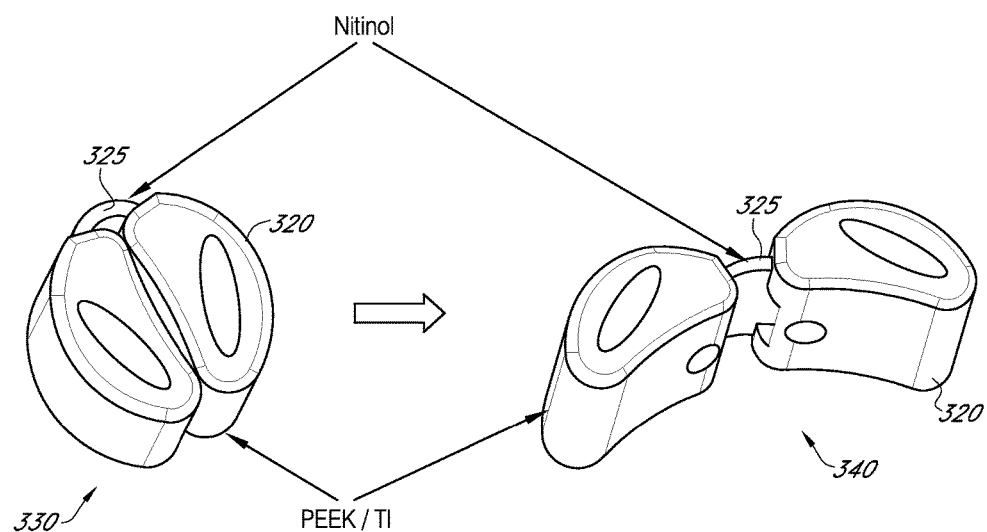
FIGS. 3E to 3F show examples of representative "mini-cages" spacers according to an example of the disclosure
Figure 3F:
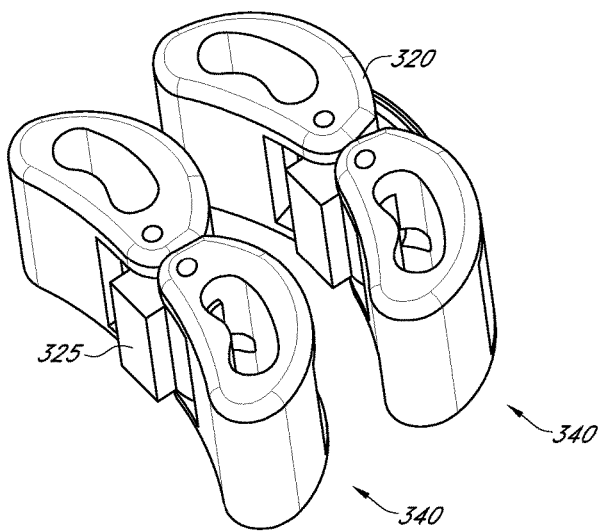
Figure 4A:
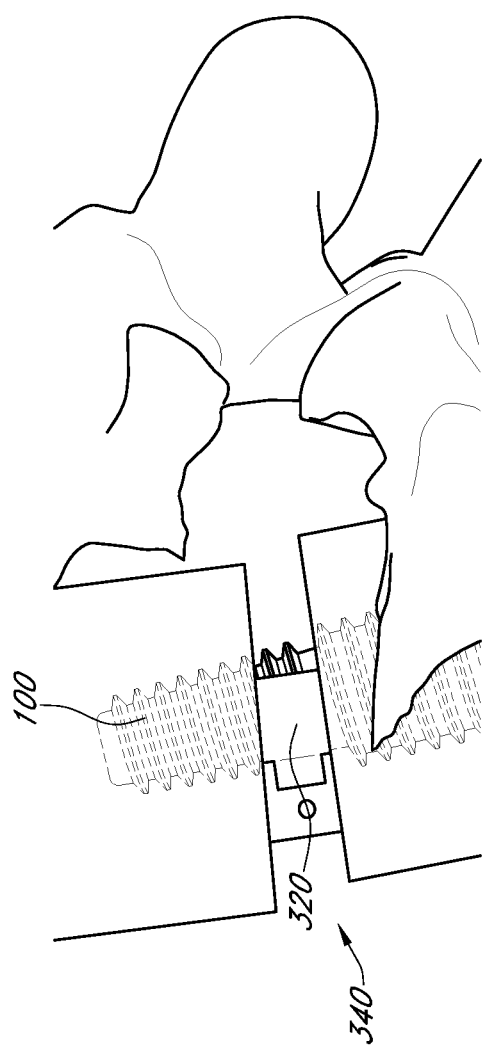
FIGS. 4A-4D illustrate examples of mini-cages/spaces deployed in conjunction with each other and with an AXI-ALIF® implant
Figure 4C:
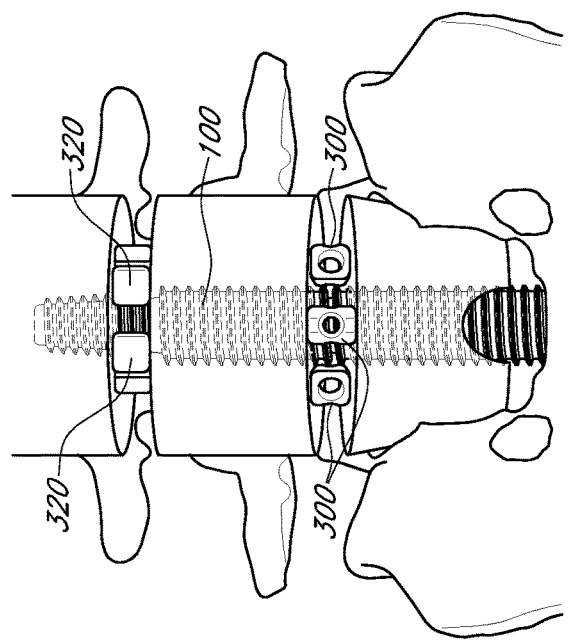
Figure 4B:
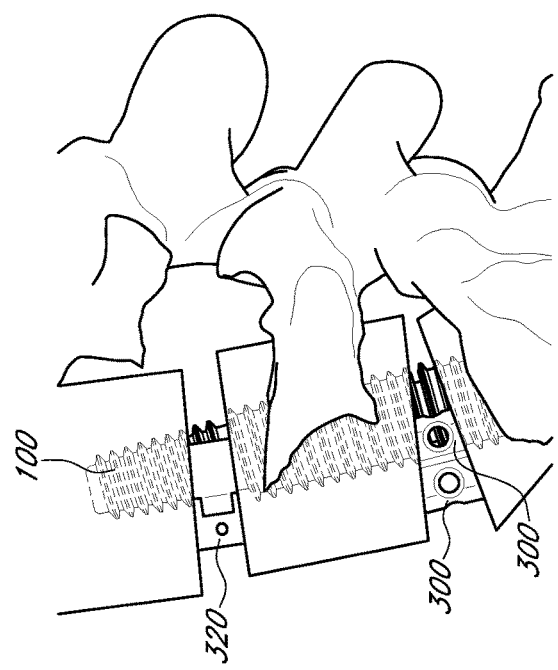
Figure 4D:
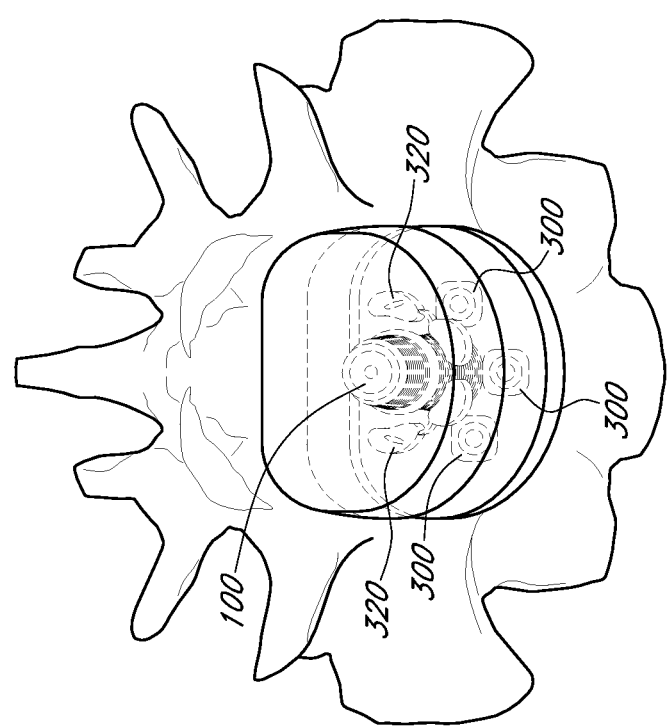

FIGS. 3A and 3B show examples of representative mini-cages/spacers. FIG. 3B illustrates the concept of deployment of a (PEEK) "spring" implant comprising, e.g., a flexible Nitinol spring. The implant is deployed through a cannula (not shown) in a compressed or folded configuration, which device expands upon emergence from the distal end of (an axial channel) insertion tool and deployment (e.g., laterally/radially) into a disc space.

FIG. 4 illustrates examples of mini-cages/spacers shown in FIGS. 3A and 3B, above deployed in conjunction with each other, at multiple spinal levels, and with an AXIALIF® implant.

FIG. 5 illustrates a wedge system comprising a plurality of wedge components and a ramped insertion tool Note that the converging point of leading edge surfaces forms a "bullet nose".

FIG. 6 illustrates the stages of insertion of one example of a wedge system.

Figure 7:
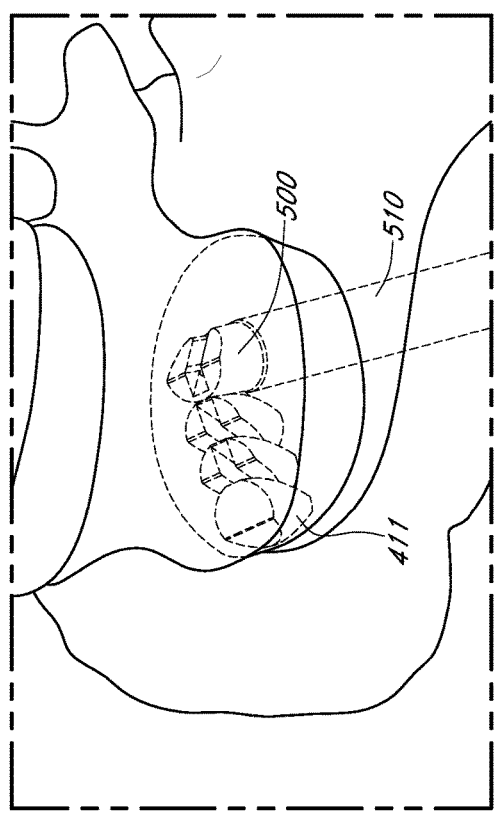
FIG. 7 shows modular wedges inserted axially through wedge system cannula with ramp insertion tool and deployed radially in disc space

FIG. 7 shows modular wedges inserted axially through wedge system cannula with ramp insertion tool and deployed laterally/radially in disc space. Note that more than one wedge construct/system may be delivered and deployed into the disc space, and including with or without an AXIALIF® implant or a sacral plug.

FIG. 8 shows each wedge component can include a wedge protrusion and/or wedge slot where each slot and protrusion are configured to complement one another.

FIGS. 9A-C illustrate a plurality of wedge components and ramped insertion tool that may be cannulated and configured to receive a retention rod.

Figure 10:
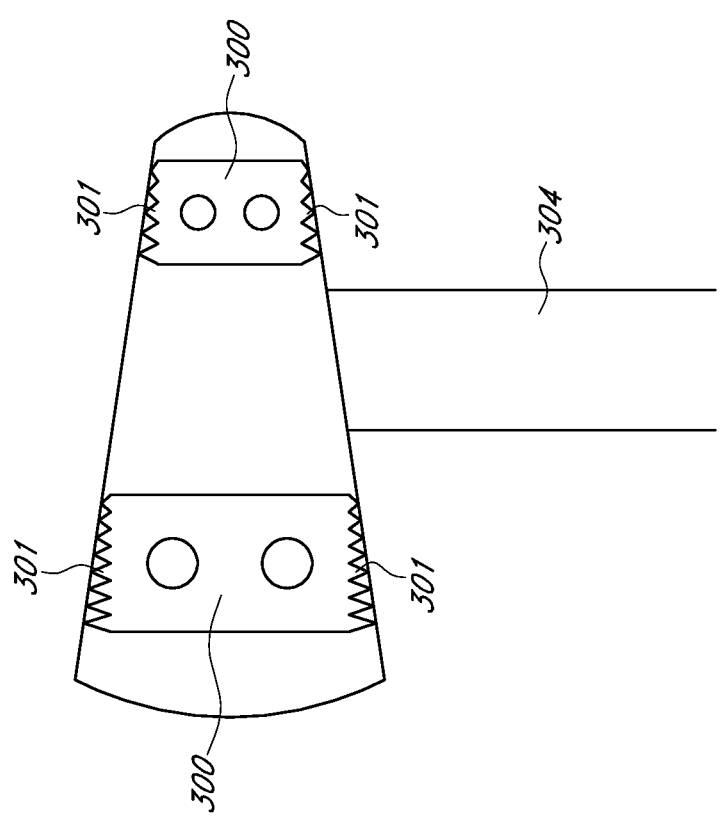
FIG. 10 illustrates a pre-sacral mini-cage "analog" to cages used in TLIF procedures
Figure 11A:
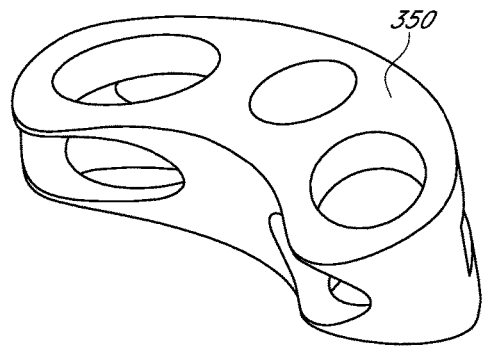
FIGS. 11A-11C depict a spinal implant that is arch-shaped to facilitate a 90° turn from axial access to lateral/radial deployment during insertion into the disc space
Figure 11B:
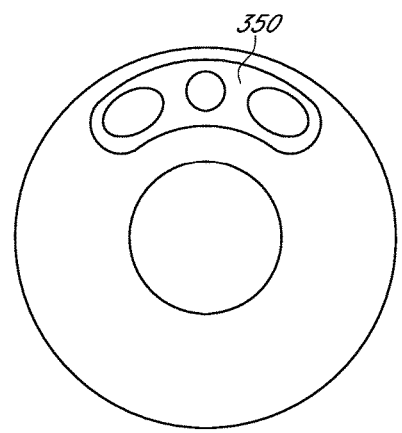
Figure 11C:
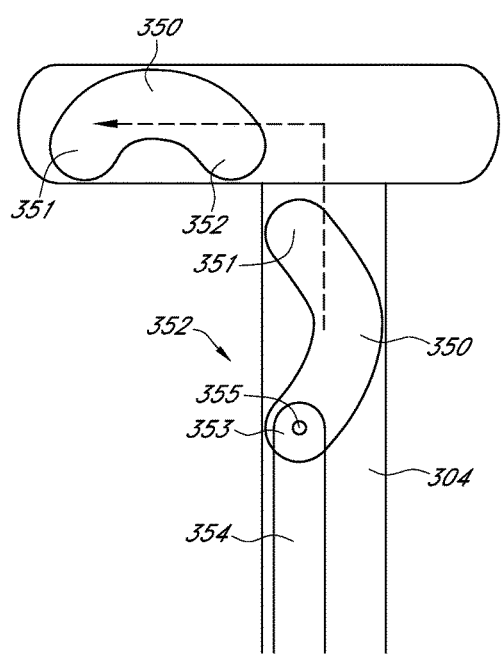

FIG. 10. illustrates a mini cage analog to cages used in TLIF procedures: a PEEK cage may be configured with "teeth" for gripping an endplate surface, as well as being configured in parallel (0 degree) and non-parallel (lordotic angles of about 0- to about 10 degrees) versions. In some examples, multiple cages may be deployed in any radial direction (anterior, anterio-lateral, lateral, posterior).

FIG. 11 depicts a spinal implant that is arch or kidney-shaped to facilitate a 90° turn from axial access to lateral/radial deployment during insertion into the disc space. In some examples, the cage is wedged (shown at top). In another example, the cage has parallel opposing top and bottom surfaces.

FIG. 12 shows stacks of multiple wafer-like implants which form constructs of varying heights to accommodate or create lordosis, and/or to achieve gradual distraction.

FIG. 13 shows a 2-piece expandable plug inserted into the sacral access bore (does not extend into disc space). In one aspect of the spinal implant system of the present disclosure, a PEEK plug is also implanted to lock the spinal cage deployed into a disc space and prevent it from migrating back out of an access channel. In another aspect and example, a plug such as depicted above may be used following a "soft fusion" procedure, e.g., where a discectomy is performed and the disc space is filled with bone graft/growth media, to prevent the graft material from "leaking" back out of the disc space. In another aspect and example, a plug is inserted following a revision surgery, for example, to remove a previously implanted AXIALIF® implant.

FIG. 14 shows a 1-piece, non-expanding plug. In some examples, a plug such as depicted above is used for purposes as described in FIG. 13, above, and also fabricated from PEEK.

FIG. 15 illustrates a 1-piece threaded cage comprising windows which carry bone graft material, and configured to maximize the device's "L-5 footprint" for axial/compressive load support and distribution.

FIG. 16 shows one example of a threaded spinal cage that is configured as an expandable "flower, e.g., with a plurality of "petals" at a distal end of the implant and shows it as it is spread as an internal metal plug comprised as part of the cage interfaces with and engages internal threads in the threaded cage, the device is advanced distally, up to but not into an inferior endplate of the L-5 vertebral body.

FIG. 17 illustrates an example of a threaded cage configured as a flower with petals similar to FIG. 16 above, but the cage is also additionally configured for insertion into L-5.

FIG. 18 shows one example of threaded cage configured as a flower with petals additionally is configured to comprise Nitinol expandable joints to improve an ability of the threaded cage to withstand repeated loading cycles.

FIG. 19 shows an example of a spinal cage configured with an angled or wedge-shaped posterior/back portion of the device. In one aspect, the device may be modularly extended, e.g., by means of in situ attachment of subsequent cages.

FIG. 20 shows an example of a cage with a non-wedged back. In this aspect, insertion of the cage is by means of a cam tool that is rotated to deploy the device into a disc space.

FIG. 21 shows a mini-cage example which is configured as an expandable device that in an expanded configuration distracts a disc space.

FIGS. 22 and 23 depict mini-cages based on, for example, a "bucky ball" concept in which a device is configured as a hollow sphere, the interior of which is filled with bone graft and the porous exterior is conducive to bone in-growth.

FIG. 24 In some examples, an individual modular cage is connected to a neighboring cage by means of a flexible wire, the flexible connection coupling the cages.

FIG. 25 shows examples of a spinal implant configured as/becomes an expanded, winged cage with radial flanges formed upon deployment. With reference to the upper row, in some examples, a "bullet nose" spinal implant with a rounded distal or leading end is compressed, forming flanges, then the implant is expanded to achieve distraction. In another example, a non-expanded device is shown (lower right hand corner, last two examples, no intermediate waist portion). In some examples, a non-expanding winged cage is delivered, for example, though S1 and partially into L5. As the cage is collapsed or compressed, wings or flanges form that are then deployed radially and support the L5 vertebrae. The implant may then be advanced fully into L5. If distraction is needed the implant can be advanced through S1 as the radial wings push on L5. In some examples, a non-distracting cage can also be inserted fully. As the cage is collapsed and wings deployed radially, the cage compresses the space. In one aspect, compression of the disc space assists in compressing the bone graft.

What is claimed is:

1. A trans-sacral spinal implant for insertion from an anterior target site on the surface of the sacrum into the sacrum, the implant comprising:
    a first body having a leading end, a trailing end, a longitudinal axis through the leading and trailing ends, a length parallel to the longitudinal axis, and a sidewall surrounding the longitudinal axis and extending from the leading end to the trailing end, the first body having an interior surface and an opposite exterior surface;
    an interior thread extending along the interior surface of the first body from the trailing end toward the leading end to a thread termination between the trailing end and the leading end;
    an exterior thread on the exterior surface of the first body;
    a second body having a leading end, a trailing end and an exterior surface extending from the leading end to the trailing end; and
    the exterior surface of the second body comprising an exterior thread that engages the interior thread of the first body;
    wherein the leading end of the first body includes at least one slot extending from the leading end of the first body towards the trailing end;
    the at least one slot extending from the exterior surface to the interior surface, the leading end forming a substantially flat distal surface that is substantially perpendicular to the exterior surface of the first body;
    wherein threading the second body into the interior surface of the first body causes the leading end of the first body to radially expand and for the threaded leading end of the second body to extend past the leading end of the first body.

2. The spinal implant of claim 1,
    wherein the leading end of the first body includes at least one slot extending from the leading end of the first body towards the trailing end,
    the at least one slot extending from the exterior surface to the interior surface,
    wherein threading the second body into the interior surface of the first body causes the leading end of the first body to radially expand.

3. The spinal implant of claim 1,
    wherein the first body comprises a plurality of distal petals.

4. The spinal implant of claim 1,
    wherein the first body comprises a plurality of distal petals, and the threading of the second body into the interior surface of the first body causes said distal petals to radially expand, providing increased surface area of substantially planar form, substantially perpendicular to said longitudinal axis of said first body; and
    said first body having a major thread diameter range of between 13 mm and 15.5 mm and a length of between 20 mm and 40 mm.

5. The spinal implant of claim 4,
    wherein a petal has length ranging between 15 mm and 20 mm.

6. The spinal implant of claim 1,
    wherein at least one of the group consisting of the first body and the second body comprises PEEK.

7. The spinal implant of claim 1,
    wherein the second body comprises metal.

8. The spinal implant of claim 1,
    wherein the first body comprises PEEK and the second body comprises metal.

9. The spinal implant of claim 1,
    wherein said exterior thread on the exterior surface of the first body comprises cancellous type bone threads.

10. The spinal implant of claim 1,
    wherein the exterior thread of the second body extends from the trailing end of the second body toward the leading end of the second body to a thread termination between the trailing end and the leading end of the second body.

11. The spinal implant of claim 10,
    wherein the interior surface of the first body further comprises a tapered form reducing toward the leading end of the first body from the thread termination.

12. The spinal implant of claim 10,
    wherein said second body further comprises a tapered form extending from the thread termination of the exterior thread of the second body to the leading end of the second body.

13. The spinal implant of claim 1,
    wherein the second body further comprises a lumen extending from the trailing end of the second body toward the leading end of the second body;
    the lumen further comprising a key for the engagement of a rotatable driver tool.

* * * * *